(12) United States Patent  (10) Patent No.: US 8,008,917 B2
Satragno et al.  (45) Date of Patent: Aug. 30, 2011

(54) MAGNETIC RESONANCE IMAGING APPARATUS

(75) Inventors: Luigi Satragno, Genoa (IT); Fabio Rezzonico, Como (IT)

(73) Assignee: Esaote, S.p.A., Milan (IT)

( * ) Notice: Subject to any disclaimer, the term of this patent is extended or adjusted under 35 U.S.C. 154(b) by 220 days.

(21) Appl. No.: 12/523,703

(22) PCT Filed: Feb. 25, 2008

(86) PCT No.: PCT/EP2008/052266
§ 371 (c)(1),
(2), (4) Date: Jul. 17, 2009

(87) PCT Pub. No.: WO2008/104522
PCT Pub. Date: Sep. 4, 2008

(65) Prior Publication Data
US 2010/0102814 A1  Apr. 29, 2010

(30) Foreign Application Priority Data

Feb. 28, 2007 (EP) ................................ 07425108

(51) Int. Cl.
*G01V 3/00* (2006.01)
(52) U.S. Cl. .................................................. 324/318
(58) Field of Classification Search .......... 324/300–322; 600/407–445
See application file for complete search history.

(56) References Cited

U.S. PATENT DOCUMENTS

| | | |
|---|---|---|
| 4,681,308 A | 7/1987 | Rice |
| 4,791,371 A | 12/1988 | Krol |
| 5,085,219 A * | 2/1992 | Ortendahl et al. ............ 600/422 |
| 6,198,285 B1 * | 3/2001 | Kormos et al. ............... 324/318 |
| 6,246,239 B1 | 6/2001 | Krogmann et al. |

(Continued)

FOREIGN PATENT DOCUMENTS

DE 19736884 A1 3/1999

(Continued)

OTHER PUBLICATIONS

International Search Report (PCT/ISA/210) for PCT/EP2008/052266 dated Sep. 11, 2008.

(Continued)

*Primary Examiner* — Brij B Shrivastav
(74) *Attorney, Agent, or Firm* — Buchanan Ingersoll & Rooney PC

(57) ABSTRACT

A Magnetic Resonance Imaging apparatus having an open U- or C-shaped magnet structure, wherein the magnet structure has at least one vertical connection member for joining two horizontal wall members which lie one above the other and are supported in a cantilever fashion and in a predetermined spaced relationship by the vertical member, the vertical member being eccentrically connected to the two wall members at a side edge thereof. The horizontal wall members and the vertical member delimit the upper and lower sides and at least a vertical lateral band of a space for receiving at least one part of a patient body. The horizontal wall members also support means for generating a static magnetic field that permeates the patient receiving space. The apparatus further includes a patient table, supported in an intermediate position between the two horizontal wall members, and lies slightly above the lower horizontal wall part, the table being displaceable in at least one displacement direction, having at least one component of motion towards and/or away from the vertical connection member, and the table being rotatable about a vertical axis outside the magnet structure, i.e. outside the horizontal wall members.

23 Claims, 13 Drawing Sheets

U.S. PATENT DOCUMENTS

| | | |
|---|---|---|
| 6,346,814 B1 | 2/2002 | Carrozzi et al. |
| 6,377,830 B1 | 4/2002 | Carrozzi et al. |
| 6,806,712 B2 * | 10/2004 | Akgun .................. 324/318 |
| 7,844,318 B2 * | 11/2010 | Rezzonico et al. ........... 600/410 |
| 2001/0012914 A1 | 8/2001 | Kuth et al. |
| 2004/0133097 A1 | 7/2004 | Bonutti |
| 2004/0257081 A1 | 12/2004 | Hahn et al. |
| 2005/0187460 A1 | 8/2005 | Persoons et al. |
| 2005/0275402 A1 | 12/2005 | Campagna |
| 2007/0282192 A1 | 12/2007 | Rezzonico et al. |
| 2008/0045830 A1 | 2/2008 | Rezzonico et al. |
| 2008/0191696 A1 | 8/2008 | Van Der Burgt |

FOREIGN PATENT DOCUMENTS

| | | |
|---|---|---|
| EP | 0995397 A2 | 9/1999 |
| JP | 2-021846 A | 1/1990 |
| JP | 2000-232969 A | 8/2000 |
| JP | 2001-128955 A | 5/2001 |
| JP | 2006-020709 A | 1/2006 |
| WO | WO 2005/096927 A | 10/2005 |
| WO | WO 2006/131863 A | 12/2006 |
| WO | WO 2007/004145 A2 | 1/2007 |

OTHER PUBLICATIONS

Written Opinion (PCT/ISA/237) for PCT/EP2008/052266 dated Sep. 11, 2008.

* cited by examiner

MAGNETIC RESONANCE IMAGING APPARATUS

The invention relates to a Magnetic Resonance Imaging apparatus having an open U- or C-shaped magnet structure, wherein the magnet structure has at least one vertical connection member for joining two horizontal wall members which lie one above the other and are supported in a cantilever fashion and which horizontal wall members are held in a predetermined spaced relationship by said vertical member, the latter being eccentrically connected to said two wall members, particularly at a side edge thereof.

The said horizontal wall members and the said vertical member delimits the upper and lower sides and at least a vertical side band of a patient receiving space for receiving at least one part of a patient body, which patient receiving space has three open sides: one frontal open side along the side edges of the horizontal wall members on the side of these horizontal wall members which is opposed to the side at which the vertical wall member is provided, and two lateral open sides respectively along the edges of each of the two opposite sides of the said horizontal wall members which are oriented transversally to the said frontal open side of the patient receiving space.

The said horizontal wall members also support means for generating a static magnetic field that permeates said patient receiving space.

The apparatus further comprises a patient table, supported in an intermediate position between the two horizontal wall members, and lying slightly above the lower horizontal wall member. The patient table having a bridge like construction comprising a length which is greater than its width and two opposite ends at each one of which an upright supporting element is provided.

The table is mounted with one end to the corresponding upright supporting element in a rotatable way around a vertical axis intersecting a longitudinal axis of the table, the upright supporting element on the opposite end of the table being slidable relatively to the ground along a circular path corresponding to the rotation of the table around the said vertical axis.

The upright supporting element which supports the table in a rotatable manner having means for being secured in a fixed relative position relatively to the magnet structure and in which position the extension of the lower wall member between the two edges along the two opposite lateral open sides of the patient receiving space and the distance from the upright supporting element which supports the table in a rotatable manner is less than the length of the patient table between the two upright supporting elements.

The said patient table is rotatable relatively to the magnet structure with its longitudinal axis oriented transversally relatively to the two lateral open sides of the patient receiving space and to the edges of the horizontal wall members along which the said lateral open sides are provided and each end of the patient table with the corresponding upright supporting element lying outside of the magnet structure and of the patient receiving space on one of the lateral open sides of the patient receiving space.

An intermediate part of the table lies over the lower horizontal wall member and the said intermediate part of the patient table.

The extension of the upper and lower horizontal wall members in the direction of cantilever from the vertical wall member or in a direction transverse to the frontal open side of the patient receiving space is greater than the width of the said intermediate part of the patient receiving space.

A limited region of the patient receiving space forming an imaging volume in which the static magnetic field has certain desired values of homogeneity, the said limited region having a predetermined position inside the patient receiving space and a predetermined distance from the vertical wall member and from the edges of the horizontal wall members at the lateral and at the frontal open sides. The patient table having one or more receptacles for holding and/or connecting receiving coil supports and/or one or more compartments for connecting and/or holding receiving coils.

Such apparatus are known, for example, from patent application DE 197 36 884. A patient table is placed in a fixed position relatively to a MRI apparatus. The table is slidable along its longitudinal axis and furthermore it is supported at one end, which is the end next to the lateral side of the MRI apparatus in a rotatable way around a vertical axis. The MRI apparatus has a magnetic structure which has a patient receiving space being opened on two lateral sides and on a frontal side, so that by rotating the patient table around the vertical axis the patient can be inserted in the patient receiving space of the MRI apparatus.

In the MRI apparatus disclosed in EP 995 397 by the applicant hereof, the table is composed of two articulated parts, one part being the lower horizontal wall delimiting the patient receiving space. Such wall is stationary and also acts as an outer cover for the lower pole piece of the magnet structure. This stationary part of the patient table has a circular plan shape which forms at least three of the edges of said wall at three open sides of the magnet structure. The other part of the patient table is a radial extension of such stationary part, with reference to a central or approximately central vertical axis of such lower horizontal wall of the magnet structure. Such second part of the patient table is fixed to the stationary part in such a manner as to slide there around along an arched guide which is concentric or substantially concentric with the central vertical axis of such lower horizontal wall. Thus, angular oscillation of the movable part, in combination with the stationary part, provides patient tables having different orientations in the horizontal plane.

Further embodiments, such as those known from EP 05729495.1, by the applicant hereof, disclose a patient table that is or can be connected to a wall of the magnet structure, e.g. said lower horizontal wall, by means of sliding guides that allow translation of the patient support surface along the longitudinal direction of such surface and the transverse direction of such surface, said direction being generally oriented with at least one component in the direction of the above mentioned vertical connection member for joining the two horizontal wall members that form the magnet structure.

While these configurations prove to be effective, they are still complex in terms of construction, thereby involving high costs. Furthermore, the displacement means are inside or very close to the patient receiving space, wherefore these means may cause imaging noise and/or have to be constructed with particular arrangements to prevent interferences with the imaging process. A further advantage is that in both cases, the MRI apparatus, i.e. the magnet structure is part of the patient table and has to at least partially support the patient's weight. This requires an accordingly sturdy and solid construction not only of the magnet structure, which is generally rather massive, but especially of the cover wall elements designed to form the patient table part and/or the table displacement guides. Last but not least, such apparatus have considerable space requirements to allow rotation and/or translation of the patient table as required by the various MRI positions for imaging different anatomic regions of patients. To reduce such space requirements, the current trend is to minimize the length and width of the patient table or the part thereof projecting out of the patient receiving cavity defined by the magnet structure. However, these arrangements have little effect on the overall reduction of the space required for patient table handling and are inconvenient for both the patient and the personnel.

The invention addresses the problem of providing a combination MRI apparatus and patient table which, using a simple and inexpensive construction, provides easy and fast patient access both to the table to take place thereon and to the patient receiving space of the MRI apparatus when the patient is on the table. The particular purpose is to allow easy and quick positioning of the patient and the receiving coils relative to the patient receiving cavity and to the imaging volume, which occupies a restricted portion of the overall cavity volume. The above shall be preferably obtained without involving higher size and construction requirements for the patient table, the magnet structure and the whole assembly, and without involving any higher cost, but a reduction of such costs.

The invention fulfils the above objects by providing a Magnetic Resonance Imaging apparatus as described above and in which the upright supporting element supporting the table in a rotatable manner being placed relatively to the vertical wall element and to the frontal open side of the patient receiving space at such a distance from the said vertical wall member that it can be displaced angularly against the vertical wall element till to an angular position in which when the longitudinal side edge of the table oriented towards the vertical wall member abuts with the said vertical wall member the longitudinal lateral side edge of the table opposed to the vertical wall member is still at least within the vertical projection of the imaging volume on the said table.

Further, at least some of said receptacles for holding and/or connecting receiving coil supports and/or said compartments for connecting and/or holding receiving coils, particularly for the receiving coils associated to limbs or anatomic regions on both right and left sides of the patient, and the receiving coils mounted or fitted in the receptacles for holding and/or connecting receiving coil supports and/or said compartments for connecting and/or holding receiving coils are positioned aligned along an axis perpendicular to the longitudinal axis of the patient table and or along a path having the shape of an arc or of a circle concentric with the vertical axis of rotation of the patient table which path passes through at least a portion of the imaging volume.

The patient table is rotatable away from or towards the vertical connection member, the vertical axis of rotation being provided in the area of one of the patient table ends, such axis being coincident with the longitudinal axis of the patient table and/or with an axis parallel to said longitudinal axis and an intermediate angular position of the patient table being provided, in which such longitudinal axis and/or such axis parallel to the longitudinal axis of the patient table passes through the central vertical axis of the imaging volume and/or the body receiving cavity and/or one or both horizontal wall members, whereas the patient table pivots beyond such intermediate position through a predetermined angle in the direction of such vertical connection member, so that the imaging volume contains a region of the longitudinal side band of the patient table support surface, which is on the side of the longitudinal axis of the patient table or an axis parallel thereto opposite the one facing toward the vertical member.

In a preferred embodiment, the patient table has a longitudinal extension greater than the corresponding extension of the horizontal plates and comprises a bridge structure with members for supporting the patient bearing surface at the two opposite end portions outside the magnet structure, the patient bearing surface being rotatable with or relative to the support member about the axis of oscillation at one of the two opposite ends and the support members on the other end including slides, carriages or the like, which are designed to slide freely or on correspondingly shaped guides along a curved path concentric with the axis of oscillation.

Advantageously, such support members are vertical support members and are provided at the two opposite end portions, and at such a distance that, when the patient table is interposed between the horizontal plates, each of said vertical support members is located on one side of two opposite sides of the magnet structure, said vertical members being situated at such a fixed or adjustable distance that the patient bearing surface is above the lower horizontal wall member.

According to yet another advantageous embodiment, the member for supporting the patient bearing surface is rotatable with said surface or said surface is rotatable relative to said vertical support member with respect to the vertical axis of oscillation, said vertical support being however fixed in position with respect to the magnet structure or possibly displaceable by displacement means and fixable in position by means for switching off or locking the displacement means or by position lock means.

The patient bearing surface has one or more receptacles for holding and/or connecting receiving coil supports and/or one or more compartments for connecting and/or holding receiving coils and at least some of said receptacles for holding and/or connecting receiving coil supports and/or said compartments for connecting and/or holding receiving coils, particularly for the receiving coils associated to limbs or anatomic regions on both right and left sides of the patient, are in such positions that the receiving coils are adjacent on an axis parallel to the transverse axis of the patient table and perpendicular to the longitudinal axis of the patient table and are coincident with a path having the shape of an arc of a circle concentric with the vertical axis of oscillation of the patient table which path passes through at least a portion of the imaging volume.

Advantageously, the vertical axis of rotation of the patient table passes through a point of the central longitudinal axis of the patient table. In the configuration in which the central longitudinal axis of the patient table is coincident with or parallel to the axis that joins the vertical axis of oscillation of the patient table and the central vertical axis of the patient receiving space and/or the imaging volume, the axis that ideally joins said vertical axis of rotation of the patient table to said central vertical axis of the imaging volume or the patient receiving space and/or said central longitudinal axis of the patient table is at a distance from the vertical connection member for joining the two plates which is greater than half the width of the patient table at the portion of said patient table which is interposed between the horizontal wall members, whereby the patient table is designed to pivot freely towards the vertical connection member beyond said position in which the central longitudinal axis of the patient table is coincident with and parallel to the axis that joins the vertical axis of oscillation of the patient table to the central vertical axis of the patient receiving space and/or the imaging volume.

Particular advantages derive from the configuration in which the central longitudinal axis of the patient table and the axis that ideally joins said vertical axis of oscillation of the patient table to said central vertical axis of the imaging volume, form an angle of oscillation towards or away from the vertical member of the magnet structure such that, with a patient lying on the table with the upper and lower limbs in normal positions and/or slightly opened apart, such oscillation allows to move from a centered position of the anatomic region of the outermost upper or lower limb in the imaging volume to a centered position of the same anatomic region on the innermost upper and/or lower limb, i.e. closer to the vertical connection member of the magnet structure.

According to the invention, either in combination with the above features or separately there from, the length of the patient table is greater than the maximum length or to the average length of a human body.

Advantageously, the width of the patient table is also greater than the maximum width or the average width of the human body, whereas the patient table may be equipped with removable or extensible lateral width extensions and the patient may be placed in a central and/or laterally staggered position and substantially parallel to the longitudinal axis of the patient table or diagonally inclined with respect to said longitudinal axis.

The invention further relates to a method of positioning at least one portion of a patient's body part associated to a predetermined anatomic region to be analyzed within the imaging volume in a space designed to receive a patient's body or a part thereof of a Magnetic Resonance Imaging apparatus, which comprises a magnet structure for delimiting said space for receiving the patient and generating a static magnetic field in said space. The magnet structure has an open U- or C-shaped cross section, wherein at least one vertical connection member is provided for joining two horizontal wall members which lie one above the other and are supported in a cantilever fashion and in a predetermined spaced relationship by said vertical member, which is eccentrically connected to said two wall members, and particularly at a side edge thereof, and which apparatus further comprises a patient table rotatable about a vertical axis outside the magnet structure, as mentioned above.

The method of the invention comprises the steps of positioning at least part of the patient table outside the patient receiving space delimited by the two opposite horizontal wall members by pivoting the patient table about a vertical axis of rotation outside the magnet structure, said rotation occurring in a direction away from the vertical support member for the two plates.

The method further comprises positioning the patient on the patient bearing surface for imaging at least one anatomic region, particularly for imaging anatomic regions of the foot, the knee, the hand, the shoulder, the spine and the head.

Still further, the method comprises positioning the patient table in said patient receiving space for acquiring signals emitted from the anatomic region to be analyzed, by pivoting the patient table about a vertical axis of rotation outside the magnet structure, in a direction towards the vertical support member for the two opposite horizontal wall members.

The method further comprises the step of pivoting the patient table into the imaging volume for imaging one or more anatomic regions, particularly for imaging anatomic regions from the right side to the left side of the body and vice versa.

In accordance with another feature, if at least a portion of the patient table or part of the patient's body is positioned outside the patient receiving space, the angle of oscillation of the patient table between the central longitudinal axis of the patient table and the axis for ideal connection of said vertical axis of rotation of the patient table to said central vertical axis of the imaging volume is of about 50°.

Advantageously, for imaging of anatomic regions of right and/or left upper and/or lower limbs, the patient has to lie on the patient table with the upper and lower limbs in normal positions and/or slightly opened apart, and in a position in which the right and left limbs are on each side of the central median axis of the patient table respectively.

Further advantageous improvements of the apparatus and method are described in the dependent claims.

Thanks to the construction of the invention, the MRI apparatus has a very small overall size, i.e. including both the apparatus and the patient table, as compared with apparatus of the same type, i.e. for Magnetic Resonance Imaging (MRI) of anatomic regions of the foot, the knee, the hand, the shoulder, the spine and the head. Since the same apparatus has to be capable of imaging each of the two shoulders, each of the two hands and each of the two knees and the two feet, the present invention avoids the need of a relative displacement of the patient table in two different transverse directions within the plane defined by the patient table bearing surface and/or a rotation of the patient table through at least 180° with respect to the magnet structure.

The construction is simple and allows convenient access of the patient lying on the patient table. Furthermore, a very long and wide patient bearing surface may be provided without increasing the overall size, which is conversely reduced. By this arrangement, the patient may be preventively positioned on the patient table in such a position that the limb or anatomic region to be examined are substantially aligned on the circular path which brings such limb or anatomic region into the imaging volume, a few minor position adjustments being only needed in an angular and/or translational direction of the patient table, parallel to the longitudinal and/or transverse axis.

In this case, the vertical member for supporting the patient bearing surface may be fixed to said patient bearing surface by means of combinations of guides and slides, allowing relative displacement of the patient table along paths of limited length, in the longitudinal and/or transverse direction, with respect to said vertical support member.

The term limited length as used herein is intended to designate displacements of a small extent with respect to the length and/or width of the patient table, i.e. at the most, of the order of a couple of tens of centimeters in the longitudinal direction and about ten centimeters in the transverse direction of the patient table or the patient bearing surface.

Additionally or alternatively to the above features of the inventive apparatus, there may be provided a patient supporting device for Magnetic Resonance Imaging apparatus, particularly for imaging anatomic regions of the foot, knee, hand, shoulder, spine and head, which device comprises a bearing surface, i.e. a patient bearing surface which is capable of accommodating at least part, particularly the whole of the patient body, one or more receiving coils with a base or mounting feet, receptacles for removable fixation of these coils on the patient bearing surface.

In this case, according to the present invention, the receptacles of such device are situated on coil supporting elements which are separated from the patient bearing surface of the patient table and are designed to be removably attachable to or on the patient bearing surface of the patient table and are mutually interchangeable, each coil supporting element having one or more receptacles for a specific coil and/or a specific pattern of one or more coils, which receptacles can have various positions in said element and various positions with respect to the patient table in the mounted condition of the coil supporting element. Advantageously, one or at least two or more coil receptacles may be provided on each coil supporting element, having identical or different shapes and/or sizes, to receive coils of different shapes and/or sizes, specifically designed for an anatomic region to be examined and/or to fit a specific patient size.

The disclosed features and further advantageous embodiments and improvements of the above described device are subject matter of the dependent claims.

The claimed features of the MRI apparatus according to the present invention allow to obviate the problems of prior art devices and particularly provide an MRI apparatus, has reduced size and costs, the same apparatus being easily adaptable for Magnetic Resonance Imaging of different anatomic regions, particularly for anatomic regions of the shoulders, the knees, the wrists, the hands, the knees, the angles and at least part of the spine.

Thanks to the invention a Magnetic Resonance Imaging apparatus of small size is provided, allowing easy positioning of the patient on the patient table and allowing proper positioning of the body part to be examined in the imaging volume. Unlike prior art patient tables, the receiving coil receptacles are not arranged over the surface of the patient table in coincidence with the anatomic regions to be examined, but slots or seats are provided for holding and/or connecting a removable coil support element which in turn accommodates one or more different types of receptacles for one or more receiving coils. By this arrangement, the patient can remain in a comfortable position during examination of both upper and lower anatomic regions of his/her body, the coil support elements being replaceable with the one that includes the receptacle for the coil associated to the specific examination and provides the best position of said receptacle with respect to the position of the patient on the patient table, and to the position of the body part, the anatomic region or the organ to be examined.

It should be noted that the above described patient table embodiment, with the possibility of removably connecting receiving coil support elements for signals emitted from the limbs and receiving coil supports for signals emitted from portions of the spine under examination, synergistically interacts with an apparatus as described hereinbefore, in which the patient table is designed to pivot within the imaging volume. The interchangeability of the coil supports, and the possibility to select and use coil supports having different patterns of coil receptacles having different positions allows to optimize the effect of oscillation of the table so that the limb or anatomic region to be examined is carried into the imaging volume only by said oscillation, and therefore imaging of different anatomic regions may be effected on both the right and left sides of the body, using the same MRI apparatus and the same patient supporting device and limiting patient displacement relative to the imaging volume, to a very simple movement.

Additionally or alternatively to one or more of the above features, the invention further relates to a Magnetic Resonance Imaging apparatus comprising a magnet structure with a cavity designed to receive at least part of a patient body under examination or an organ or anatomic region or part thereof, in which cavity a portion is adapted for MRI functions, i.e. the so-called imaging volume, and a patient supporting device, such as a patient table, armchair or the like, which is or can be associated to the magnet structure to allow patient positioning relative to said imaging volume, in which a MRI image display is mounted directly on the magnet structure, to display the image data provided by a central unit for generating images from magnetic resonance signals.

In an advantageous embodiment, the central image generating section has a memory which stores one or more magnetic resonance imaging sequences and/or one or more imaging parameter settings, associated to such sequences, which are adapted for real time or quasi real time position imaging.

Furthermore, according to an improvement, the central image generating section comprises recall means of the software or electromechanical switch or selector type, for recalling the imaging settings and the imaging and position image display procedures, whereas one or more controls are provided on the magnet structure for recalling and/or selecting and/or implementing the procedures for acquiring and displaying the position images and/or software procedures for selection and control of the central image generating section of the menu type, and selects and actuates (by pointing and clicking) for controlling and changing the position imaging settings.

Therefore, the above Magnetic Resonance Imaging apparatus has very simple means which facilitate proper and exact positioning of the anatomic region of a patient relative to the imaging volume, and further evaluation of such positioning directly on the patient and with reference to images of said limb or anatomic region under examination. Using low resolutions, as currently selected in prior art in scout images, positioning control may be performed in quasi real time and, which is more important, without leaving the apparatus and the patient to reach the display station. In prior art Magnetic Resonance Imaging apparatus, image display and processing means are not in direct contact with the patient, wherefore each patient displacement has to be followed by a patient position check on the display means.

Further advantages consist in that, as positioning occurs by manual means and using the patient table that is displaceable relative to the magnet structure, the operating personnel can watch a real time image of the proper frame of the organ or anatomic region to be imaged. Such image is displayed over the magnet structure and does not require the operating personnel to leave the structure and reach an image display station, as required in prior art MRI apparatus. This highlights the synergistic integration of this feature with the apparatus having a pivoting patient table as described above.

The availability of a copy of the image of the region to be imaged near the apparatus and the patient is advantageous as it allows to reduce examination times, allowing for a prompt patient position check.

As mentioned above, the dependent claims disclose and illustrate further improvements and features of the invention.

Particularly advantageous is the embodiment in which the magnetic structure has the cross section of a double C or of a laid down H in which one vertical wall element is provided or two vertical elements are provided one against the other and in which the upper and the horizontal wall members protrude in a cantilever way from each side of the vertical wall element or of the two adjacent vertical elements forming two patient receiving spaces on the two opposite sides of the vertical wall element, to each one of which a patient table is associated and having one or more futures described above with reference to the simple C or U shaped magnet structure.

In this case the particular configuration allows reducing the dimensions of two MRI apparatus as it appears more clearly form figure The features of the invention and the advantages derived there from will appear more clearly from the following description of an embodiment, illustrated in the annexed drawings, in which.

Figure 1:
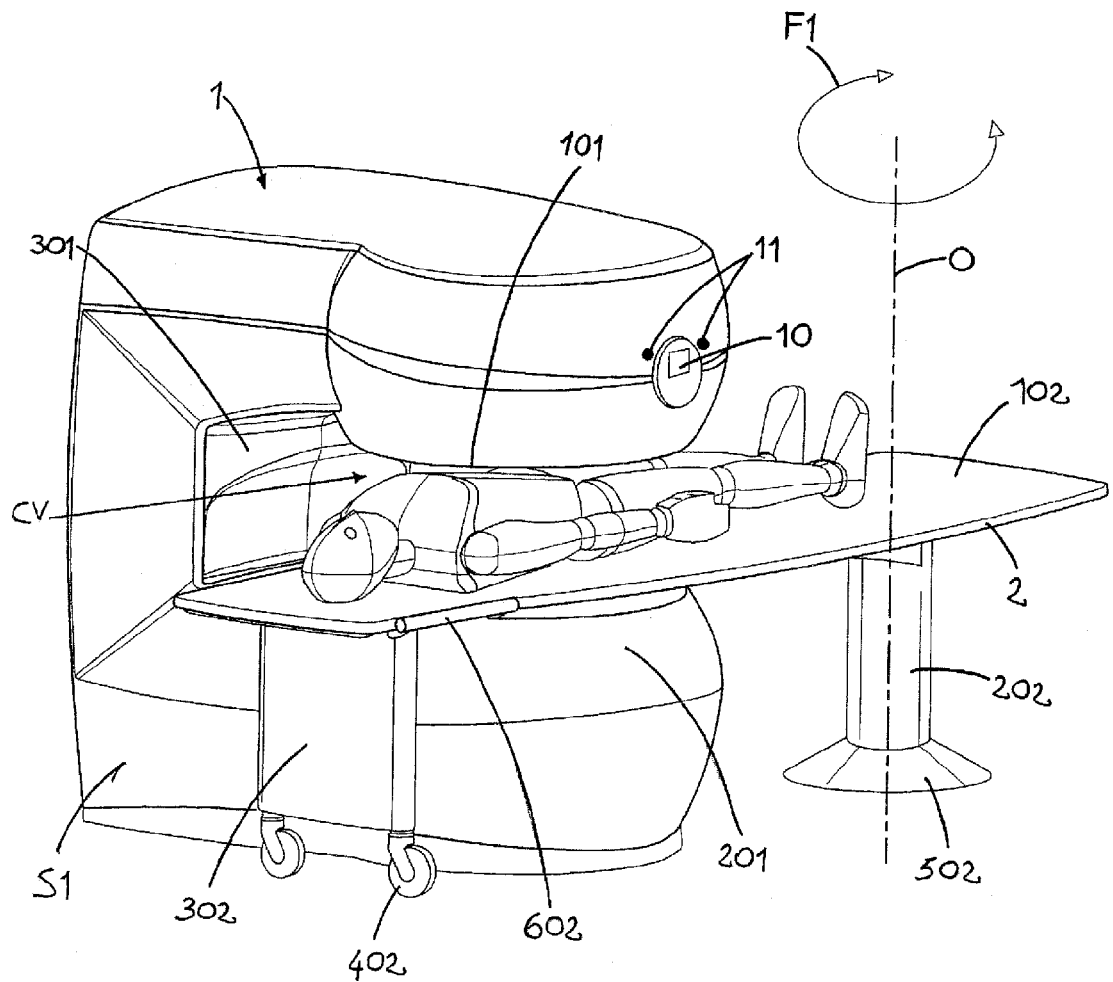
FIGS. 1 and 2 are perspective views of an apparatus of this invention, with the table pivoted to a position inside the patient receiving cavity and to a position outside such cavity and at a distance from the magnet structure respectively.
Figure 2:
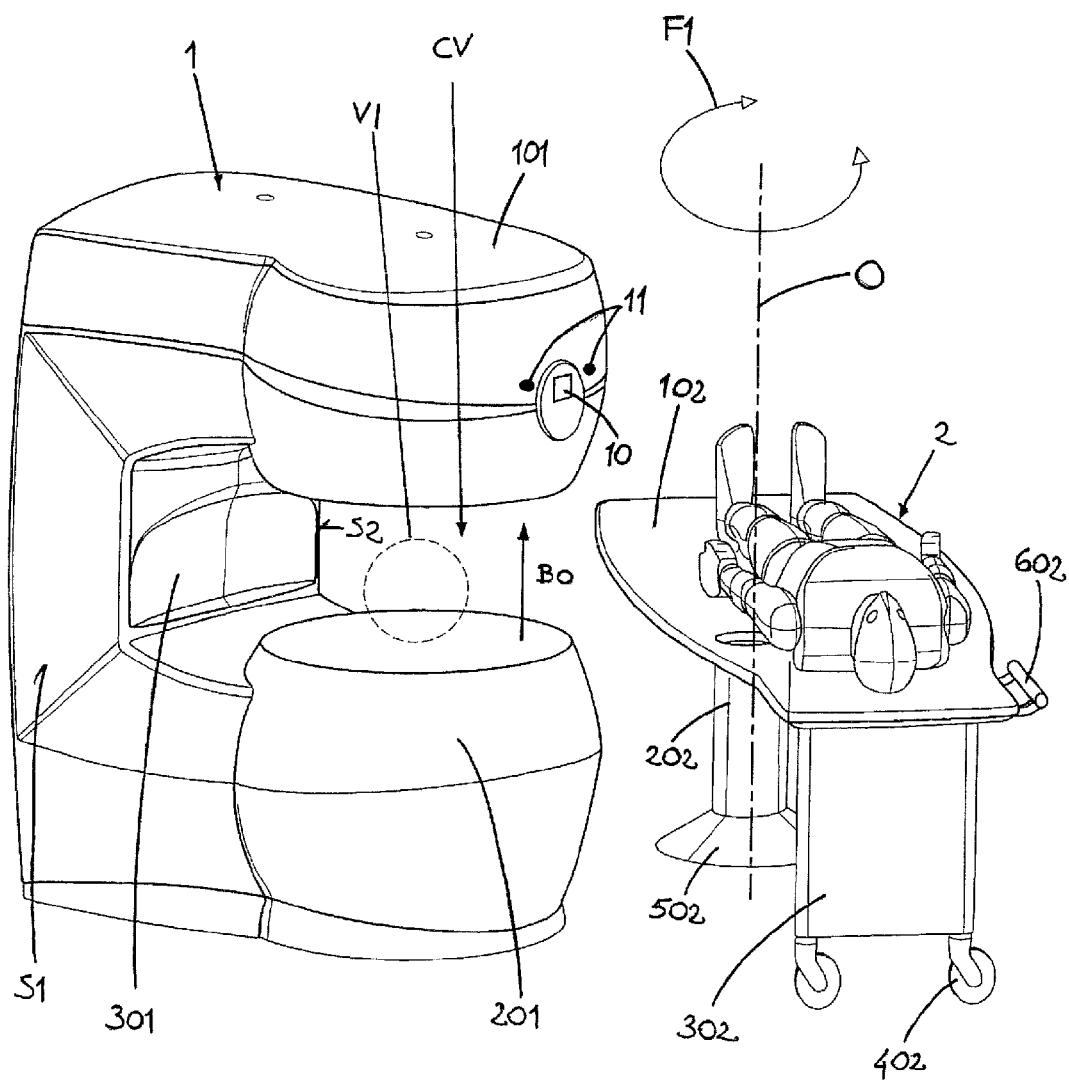
Figure 5:
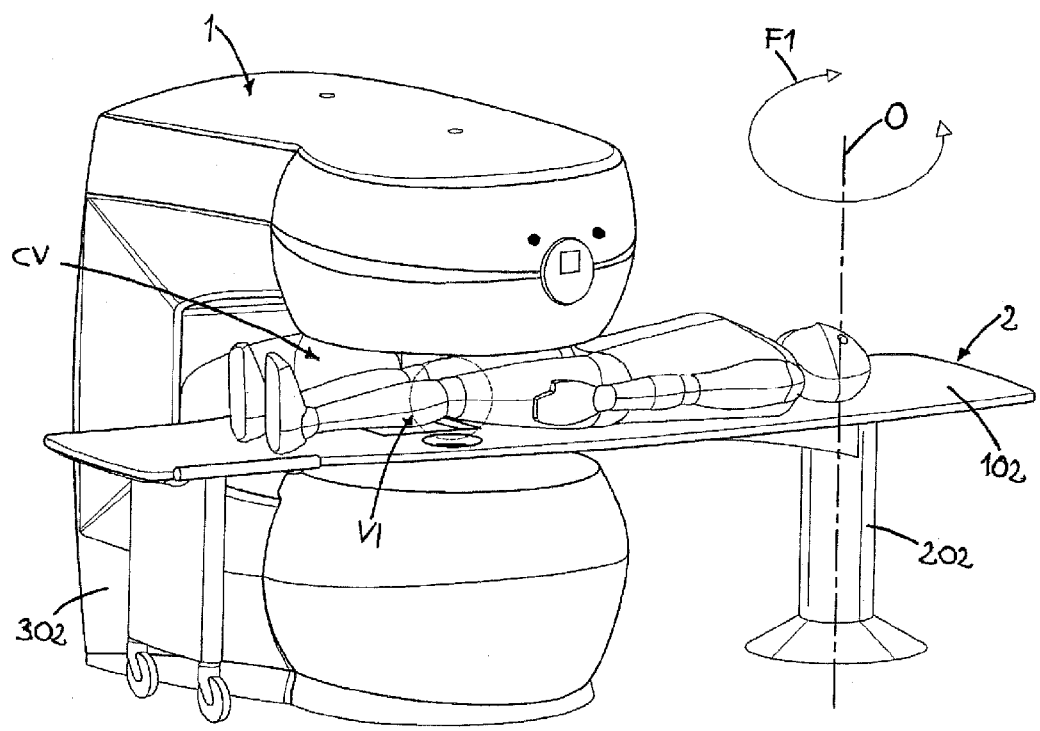
Figure 6:
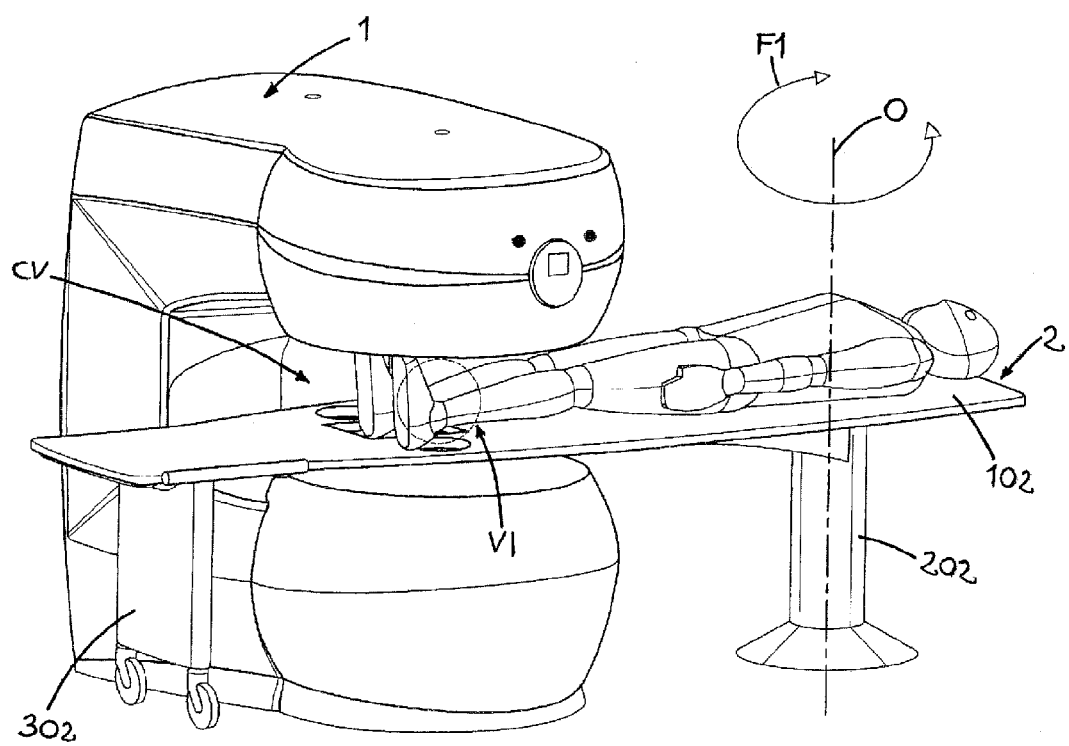

FIGS. 5 and 6 are perspective views, similar to FIGS. 1 and 2, of an apparatus of this invention in which the patient lies on the patient table and such patient table is pivoted into the patient receiving cavity so that the imaging volume contains the right knee anatomic region and the right ankle anatomic region respectively, i.e. the knee and ankle farthermost from the vertical member of the magnet structure.

Figure 7:
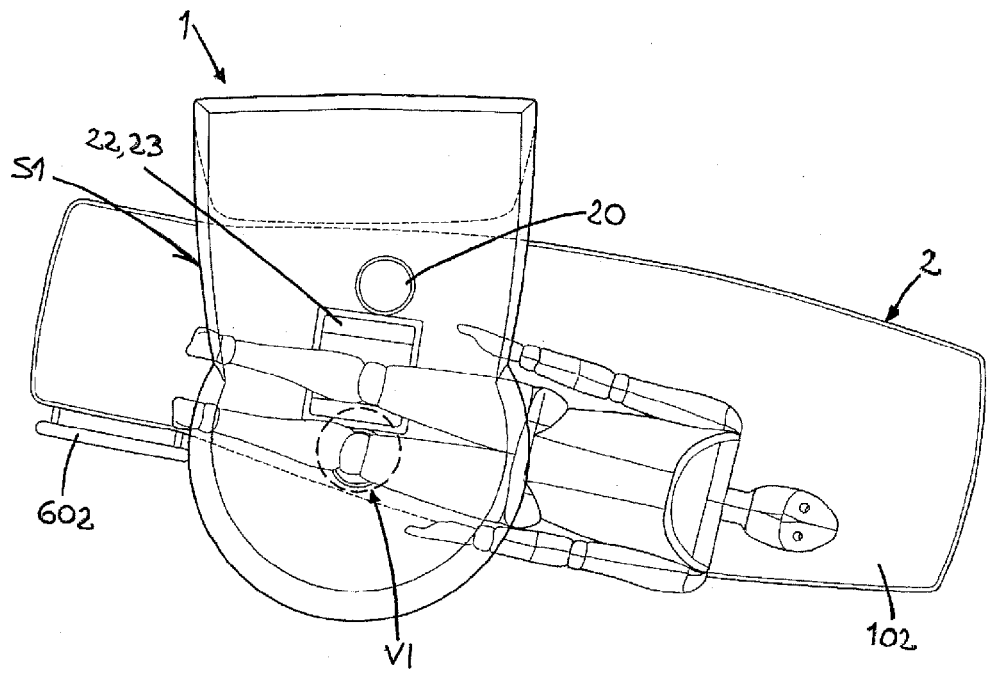
Figure 8:
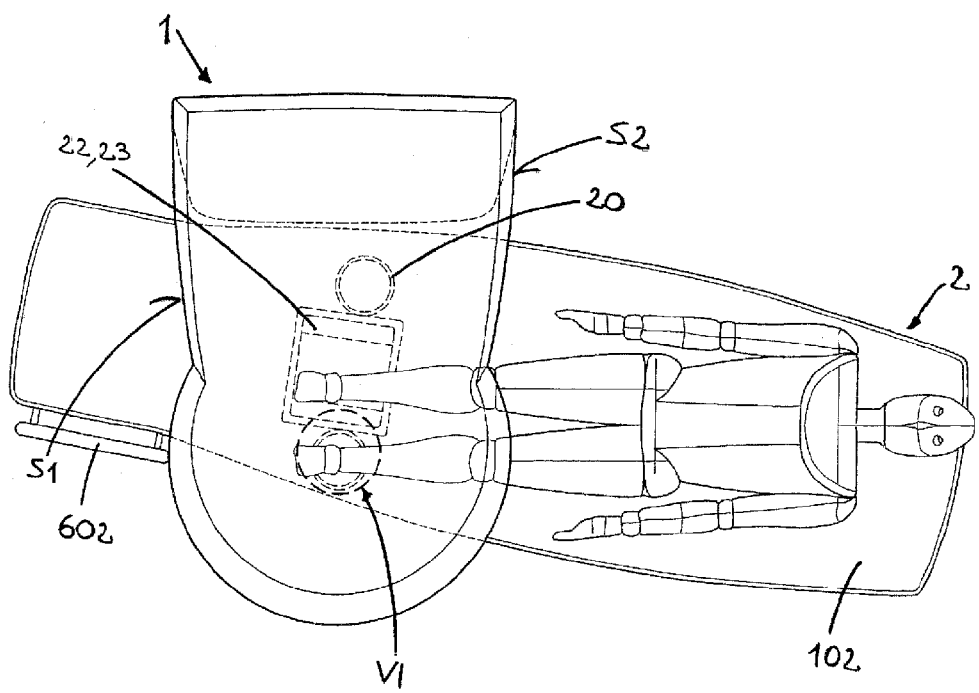

FIGS. 7 and 8 are plan views of the conditions as shown in FIGS. 5 and 6, the magnet structure and particularly the upper horizontal leg that also forms the upper horizontal wall member being shown as if they were transparent.

Figure 9:
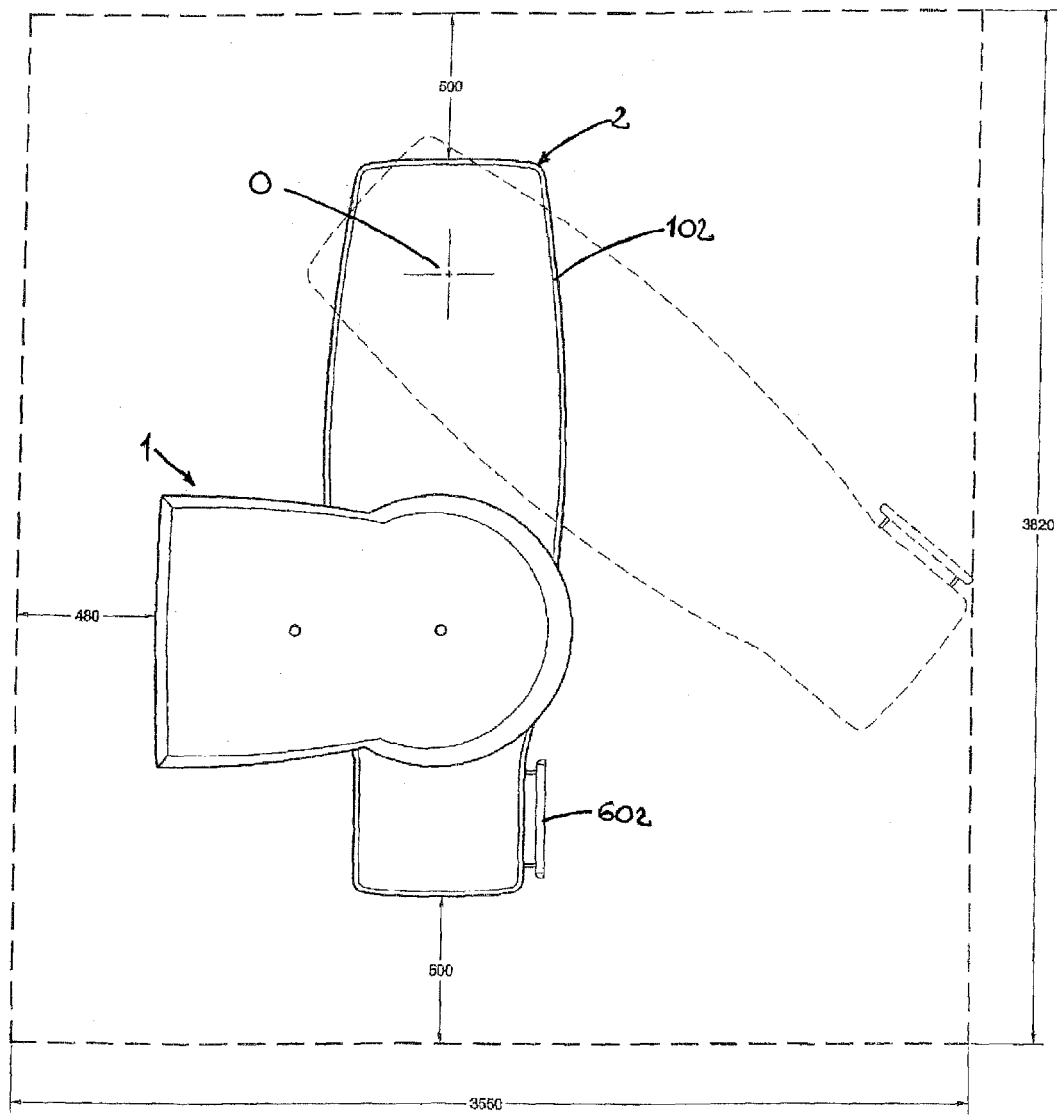

FIG. 9 is a plan view of the apparatus as shown in the previous figures, which is inscribed in a polygon having the preferred maximum size as required for such MRI apparatus.

Figure 10:
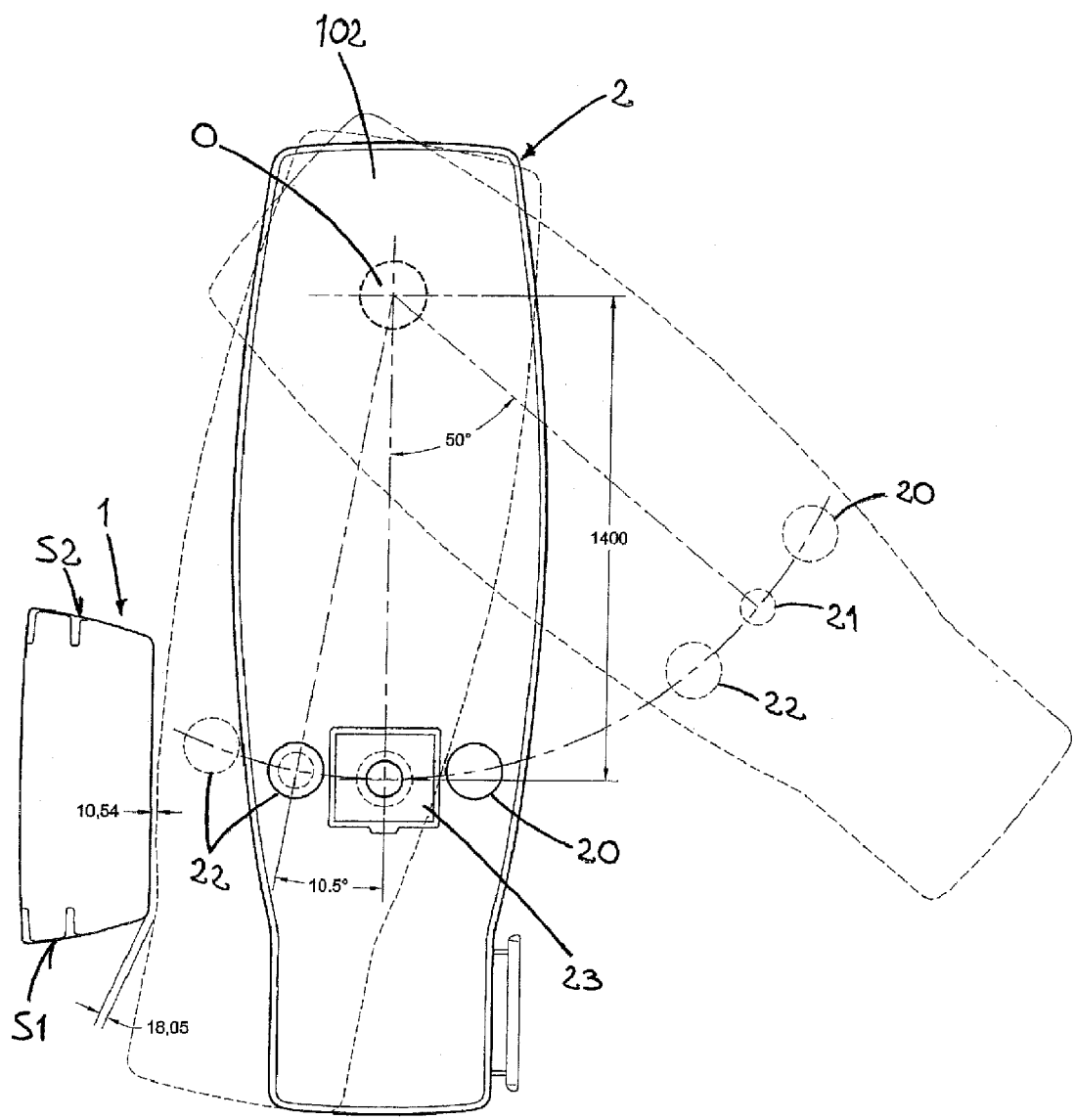
Figure 11:
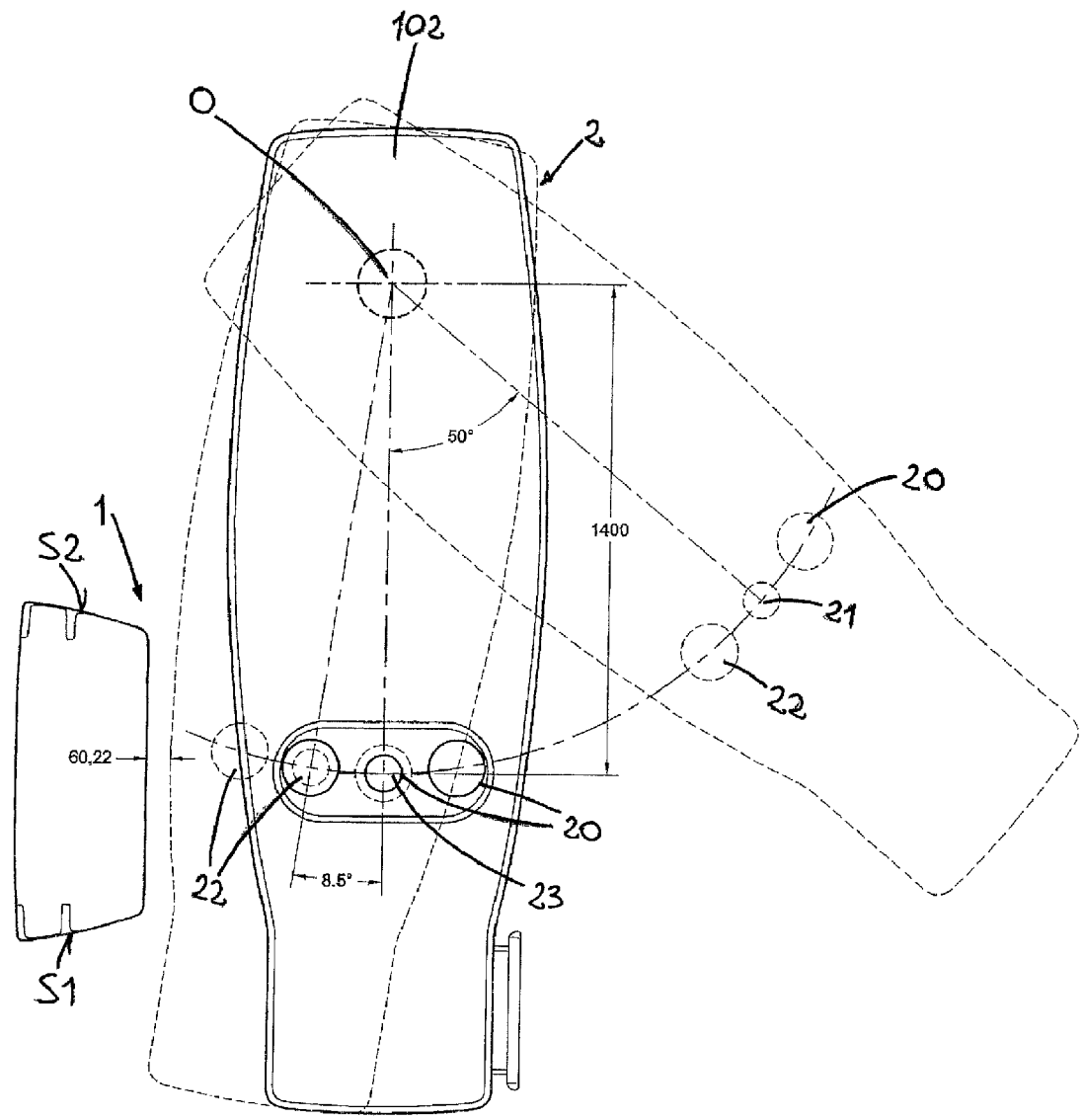

FIGS. 10 and 11 are schematic views of the oscillation path of the patient table relative to the vertical wall member of the magnet structure and a few measurements of such oscillation, as well as two different coil supporting elements, in combination with the patient tables of the two figures, each of such coil supporting elements having a different pattern of the receptacles for connection of the various coils.

Figure 12:
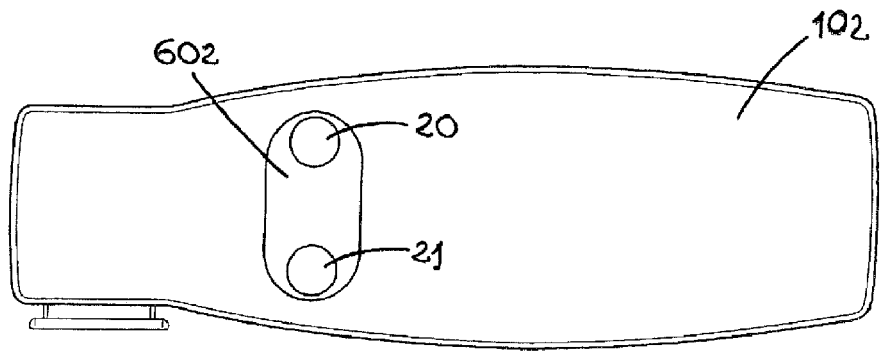
Figure 13:
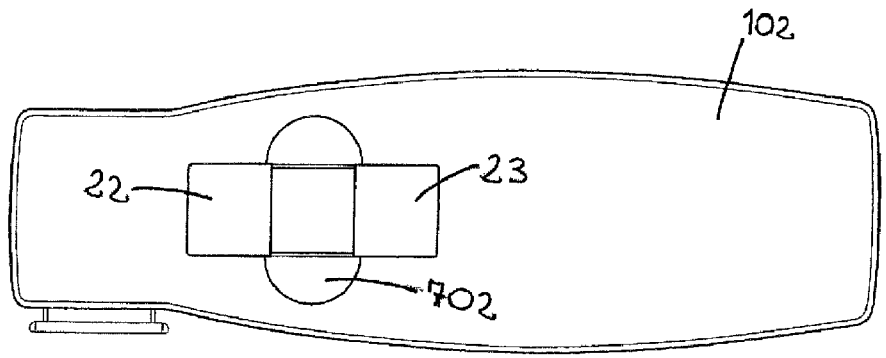

FIGS. 12 and 13 are plan views of a patient bearing surface having respective different types of coil supporting elements.

Figure 14:
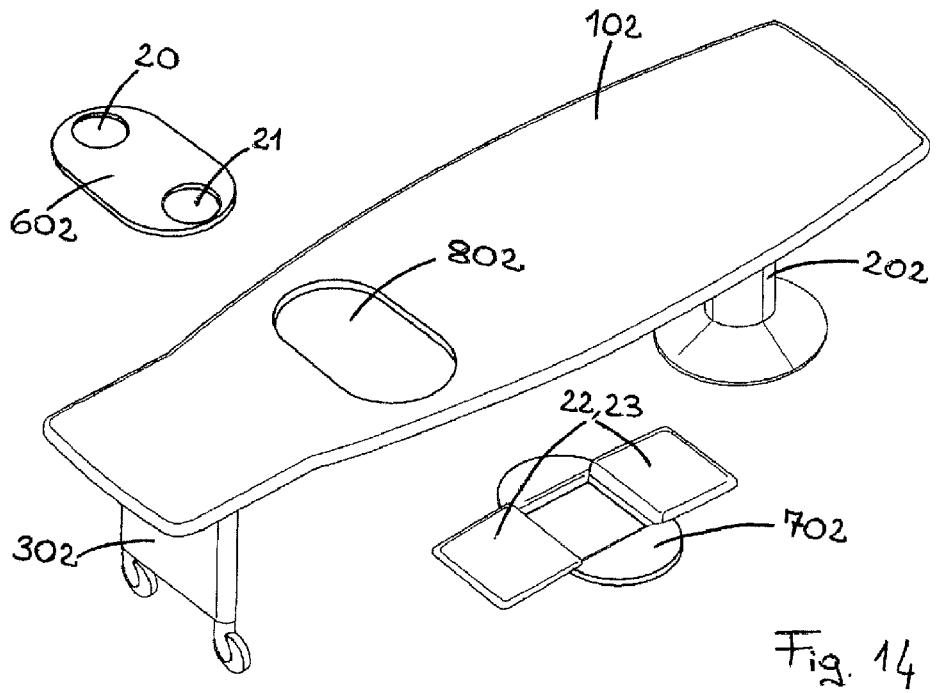

FIG. 14 is an exploded perspective view of the patient table with a patient bearing surface as shown in the previous figures and with the two different coil supporting elements of FIGS. 12 and 13.

Figure 15:
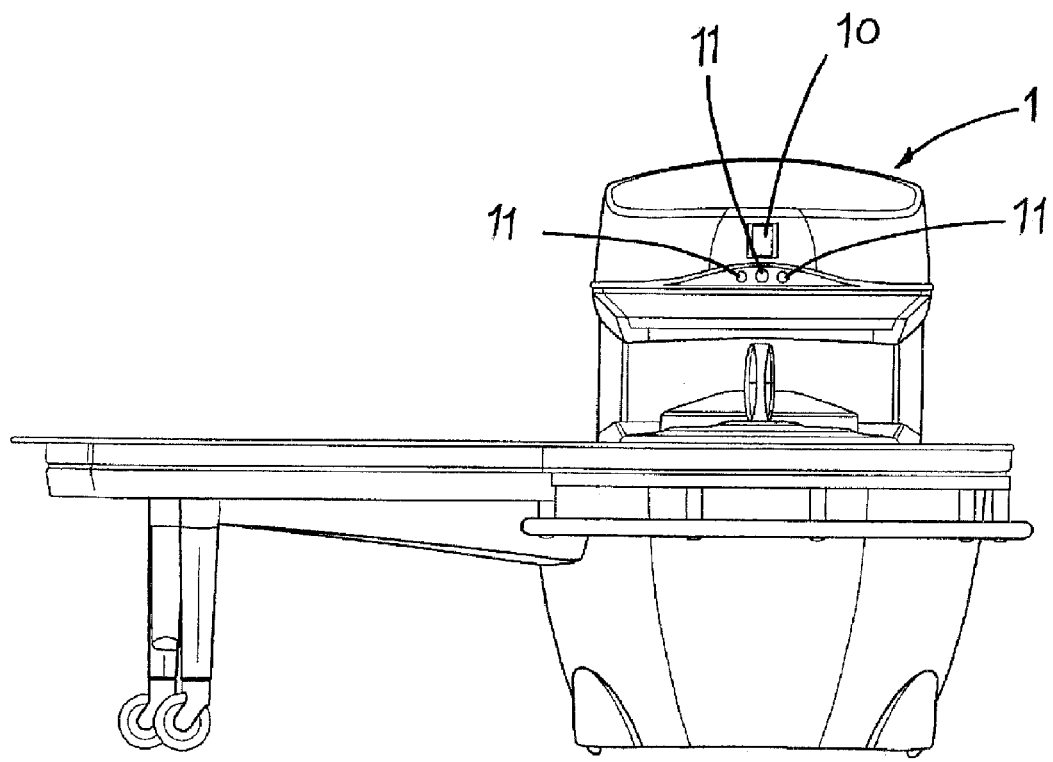

FIG. 15 shows a MRI apparatus in which a display is provided over the magnet structure and a control panel is provided for controlling predetermined functions which are directly accessible from the magnet structure and during positioning of the patient for imaging.

Figure 16:
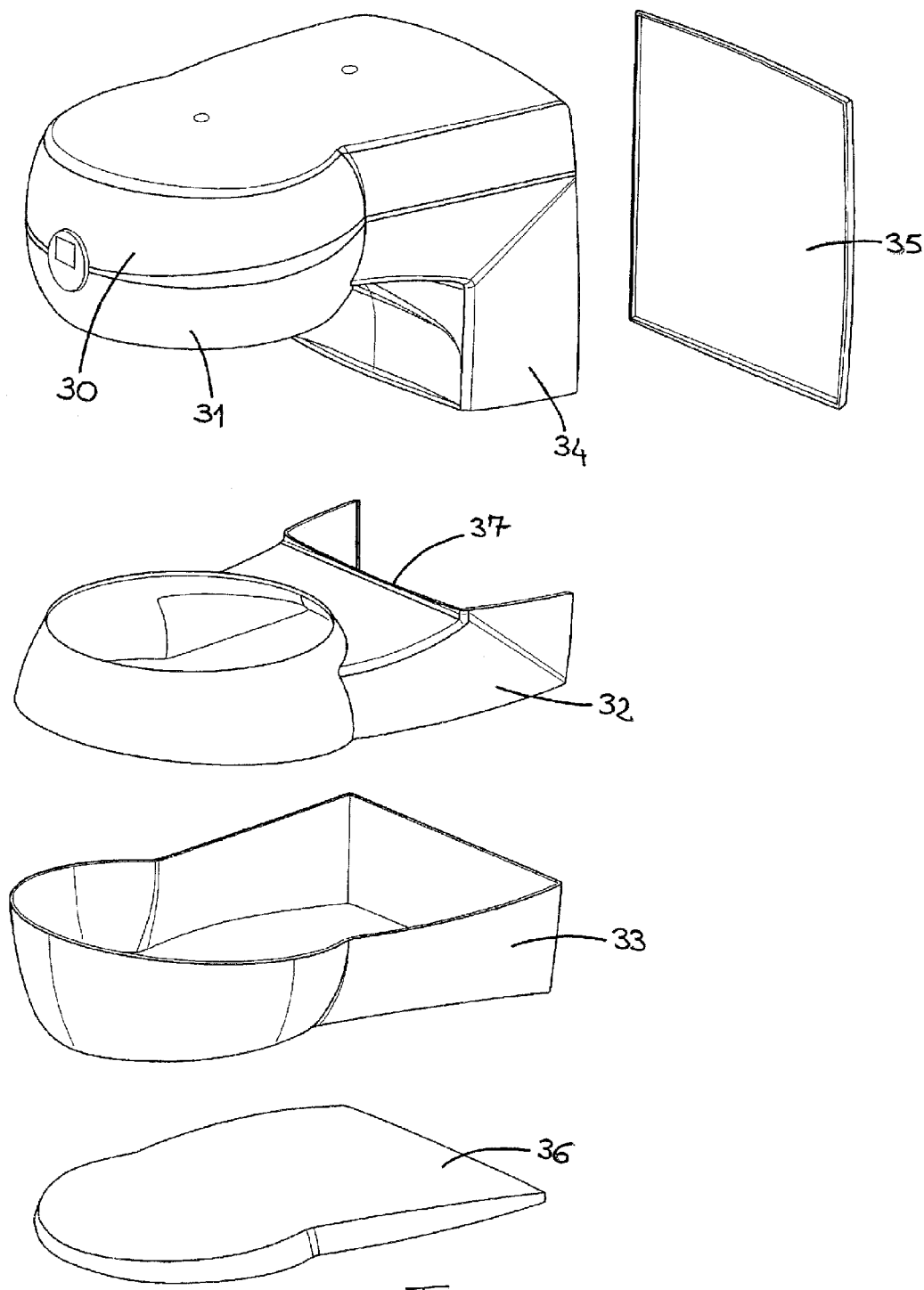

FIG. 16 is an exploded view of an external shell for the magnet structure and associated means for excitation, encoding and reception of magnetic resonance signals associated to said structure, as well as additional members associated thereto.

Figure 17:
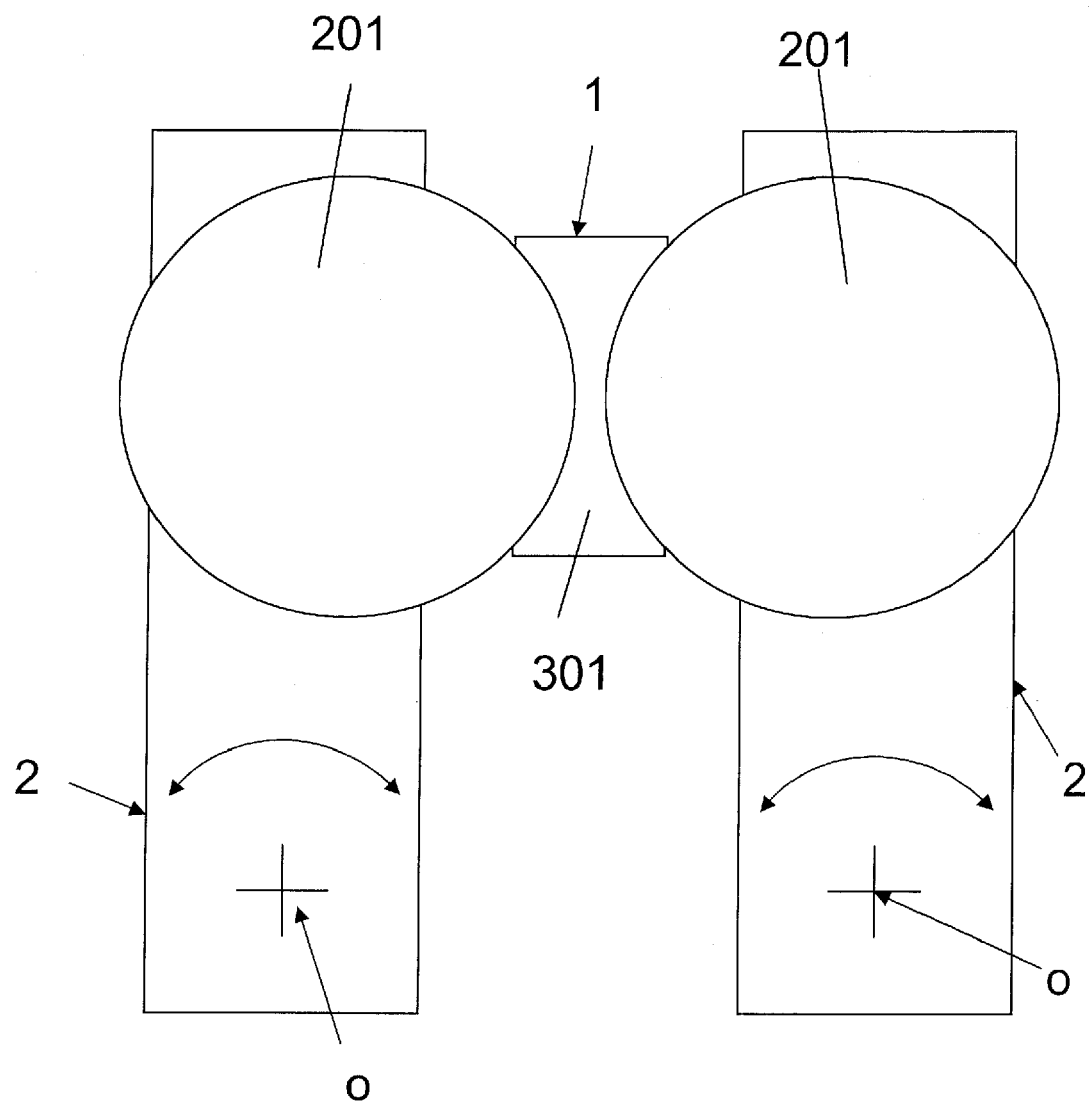
Figure 18:
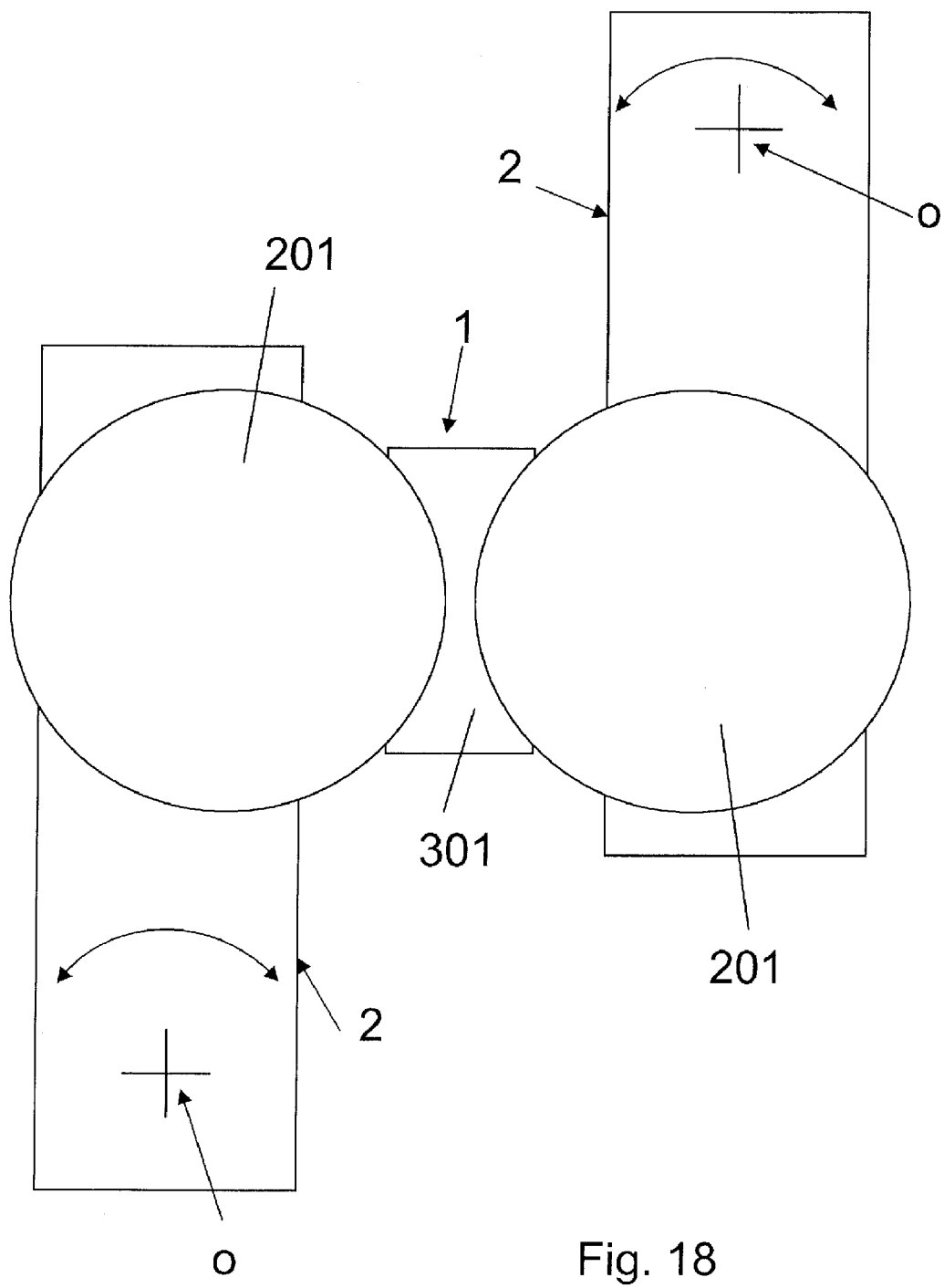

FIGS. 17 and 18 illustrate a schematic view of two variants of a further embodiment of the MRI apparatus according to the present invention in which in one device two MRI apparatus are integrated each one having the construction according to the above figures.

Referring to the figures, a Magnetic Resonance Imaging apparatus has a magnet structure 1 and a patient table 2. For simplicity, as used in the present specification, introduction and claims, the term magnet structure generally designates the yoke, the static field generating means, the pole pieces and the members normally present in such apparatus, such as gradient coils, compensation coils, electromagnetic shields, temperature measuring means and/or adjustment means and other members, as well as the outer cover of these members which, as better explained hereafter, is formed of wall members which act as outer cover shields, having functions to protect the apparatus, the patients and the users, add aesthetic value and/or fix parts that do not contribute to excitation and reception of signals wherefrom images are generated. This simplification is self-evident and unequivocally for those skilled in the art, wherefore the term magnet structure shall be considered equivalent to its pars pro toto meaning as a shape and size determining element, whereas the other elements are generally supported by such structure and only determine thickness increases and reductions of the patient receiving cavity CV.

It shall be further noted that, while reference is being made herein to a magnet structure in which the two pole pieces and the patient bearing surface have a perfectly horizontal orientation, a structure may be provided in which the pole pieces are inclined to a certain extent with respect to the horizontal plane or in which such pole pieces are not flat in shape.

Referring to the figures and to the above, the magnet structure or the magnet of a MRI apparatus has a C or open U shape with two horizontal legs spaced apart at one side by a vertical member 301. The two horizontal legs form wall members 101, 201 which delimit the upper and lower sides of a space CV in which a patient or a part thereof is received. Particularly, in the annexed figures, the two legs of the magnet structure are spaced to such an extent as to allow introduction of the patient trunk in the patient receiving space or cavity CV. These two legs are the horizontal legs of a yoke whose facing sides support magnetic field generating means, such as layers of magnetized material, pole pieces formed of ferromagnetic plates, several variable magnetic field generating coils, the so-called gradient coils, the coil for transmitting nuclear spin excitation pulses, and other operating units, such as shielding means, temperature measuring means, and other means. A static magnetic field Bo is generated between the two horizontal legs. The vertical wall member 301 is composed of a vertical yoke member and additional magnetized or ferromagnetic layers, which have the function to contribute to optimization of the static magnetic field Bo. These elements are covered by an outer protective shell, which also adds aesthetic value to the apparatus.

The static magnetic field Bo is not of optimal quality for imaging along the whole extension of the horizontal wall members 101, 201, but can achieve the desired characteristics, especially in terms of homogeneity, in a portion of the overall cavity volume, delimited by an ideal spherical or ellipsoidal surface, known as imaging volume, which is schematically shown and designated by VI in the figures.

The magnet structure is provided in combination with a patient table 2 having a substantially horizontal patient bearing surface 102, which is respectively supported at the two opposite ends by a vertical support member 202, 302. These vertical support members are spaced at a distance that is greater than the horizontal size of at least the lower leg of the magnet structure 1. Therefore, the patient table has a bridge-like structure and the patient bearing surface is above the lower horizontal wall member 201. Thus, the patient table may be introduced in the patient receiving cavity CV by moving it transverse to its longitudinal extension so that it is set astride the lower horizontal leg of the magnet structure.

Referring to the configuration of the figures, one of the members for supporting the patient bearing surface 102 is formed in such a manner as to allow such patient bearing surface 102 to pivot about a vertical axis O. This axis of oscillation is in such position as to coincide with one end of the patient table and to be situated outside the magnet structure, particularly adjacent to one of the sides of the magnet structure that are oriented parallel to a vertical section plane intersecting the horizontal legs and the vertical leg of said magnet structure and along which the legs of the C- or U-shape of said magnet structure extend.

For simplicity, these sides will be hereafter referred to as side flanks S1 and S2 of the magnet structure, whereas the other two sides will be referred to as the open front side and the closed rear side.

The axis of oscillation is in such a position as to fall within the projection of the width dimension of the upper and lower horizontal wall members 101 and 201, perpendicular to such side flanks and at such a distance from the corresponding side flank of the magnet structure that the vertical member for supporting the patient bearing surface 102 disposed at the opposite end of such patient bearing surface is adjacent to the opposite side flank S1 of the magnet structure and, during oscillation of the patient table, moves along a circular path concentric with the axis of oscillation O outside the magnet structure, thereby allowing the patient bearing surface to access the patient receiving cavity CV substantially from the open front side of the magnet structure, to carry the patient into said cavity.

In the illustrated embodiment, the axis of oscillation O is coincident with or parallel to the central vertical axis of the vertical support member 202. Such vertical support member 202 may be designed, for example, as a column on which the patient bearing surface 102 is mounted to rotate relative thereto. In this case, the foot 502 of the column is stationary or fixed to the floor. Alternatively, the vertical support member 202, i.e. the column, may be fixed to the patient bearing surface 102 and rotate therewith, the foot 502 being formed to be either rotatable relative to the floor or fixed or stationary relative to the floor, with the column 202 rotating relative thereto.

According to an alternative embodiment, the foot 502 may be formed as a carriage with wheels susceptible to be locked or retracted relative to the foot, so that such wheels may be operable or not and the foot 502 and the vertical support member 202 may be alternately movable or locked in position. This arrangement allows to easily adjust the position of the patient table and particularly of the vertical support member 202 of the patient table, as well as the vertical axis of oscillation thereof with respect to the magnet structure, wherefore the patient table may be also used in combination with magnet structures having different patterns and/or sizes.

In this case, in any combination or subcombination with the above features, the patient bearing surface 102 may be arranged to be fixed to the vertical support member 202 associated to the axis of oscillation using means for restricted displacement of said patient bearing surface 102 with respect to the vertical support member 102, which means may be combinations of guides and slides. These means may be configured to allow unidirectional translational motion, such as longitudinal to the patient table and/or parallel to the axis that joins the axis of oscillation of the patient table and the central vertical axis of the patient receiving cavity CV or the imaging volume VI. Displacement means may be further provided which also allow limited translational movements transverse to the patient table and/or perpendicular to the axis that joins the axis of oscillation of the patient table and the central vertical axis of the patient receiving cavity CV or the imaging volume VI or parallel to the direction in which the central vertical axis of the patient receiving cavity CV or the imaging volume is joined to the central axis of the vertical wall member 301 or an axis parallel to such axis.

On the other hand, the vertical support member 302 at the opposite end of the patient bearing surface advantageously has a carriage on the floor which can be integrated in or formed of the vertical support member 302 itself and, as shown, brings two or more wheels 402 or two or more wheel groups to positions that are spaced transversely to the patient bearing surface 102.

According to a further feature, the vertical support member 202 coincident or associated with the vertical axis of oscillation O of the patient bearing surface 102 of the patient table 2 may be mounted to means that connect the vertical support member 202 to the magnet structure in a fixed manner or in a displaceable manner, along paths and to predetermined positions, using translation guides that are fixed with respect to the magnet structure. In this case, the second vertical support member 302 at the opposite end of the patient bearing surface may be also mounted on a sliding guide or slide freely like in the illustrated example.

It shall be noted that the position of the vertical axis of oscillation O relative to the magnet structure uniquely determines the displacement paths of the patient bearing surface 102 with respect to the magnet structure. Therefore, means may be provided for automatic and contactless detection of the alignment position of the vertical support member 202 coincident or associated with the vertical axis of oscillation O, or other marks arranged over the patient table associated to the magnet structure, which means may include optical sensors arranged in such a pattern as to detect said marks of the patient table in two directions and/or proximity sensors or other types of sensors. In this case, a single patient table may serve multiple apparatus and be combined therewith in a quick and fast manner.

In one more embodiment, not shown, one or both the vertical support members 202 and 302 are extendable for raising or lowering the corresponding end of the patient bearing surface 102, the latter being tilted about a horizontal axis oriented in the direction of the width of the patient bearing surface.

Additionally or alternatively to one or more of the above features, the patient bearing surface 102 may be also fixed to the vertical support members 202, 302 using means for pivoting such surface about a longitudinal axis of the patient table, which may be the central longitudinal axis or an axis parallel thereto.

In the preferred configuration of the figures, the width and shape of the patient table and the patient bearing surface 102 within the transverse band aligned or coincident with the patient receiving cavity CV and/or with the vertical wall member 301 is such that the patient bearing surface may be pivoted in the direction of the vertical wall member 301 through a certain angle beyond the position in which the central longitudinal axis of such patient beating surface 102 is coincident with the axis that joins the vertical axis O of oscillation of the patient bearing surface to the central vertical axis of the patient receiving cavity CV and/or the imaging volume VI and/or the extension of the ferromagnetic plates that foam the pole pieces of the magnet structure.

This feature is well shown in FIGS. 7 and 8 and in FIGS. 9 to 11. Still referring to the preferred embodiment of the figures, the position of the vertical axis of oscillation O with respect to the magnet structure 1 is selected so that the axis that joins said vertical axis of oscillation O of the patient bearing surface and the central vertical axis of the patient receiving cavity CV and/or the imaging volume VI and/or the extension of the ferromagnetic plates that form the pole pieces of the magnet structure is perpendicular to the central vertical axis that intersects the two horizontal legs and the vertical leg of the magnet structure.

Furthermore, in this specific case, the vertical wall member 301 is substantially parallel to said axis that joins said vertical axis of oscillation O of the patient bearing surface and the central vertical axis of the patient receiving cavity CV and/or the imaging volume VI and/or the extension of the ferromagnetic plates that form the pole pieces of the magnet structure.

It shall be noted that, while this configuration is aesthetically valuable and provides construction advantages in terms of symmetry and strength, the inventive concept is not limited thereto.

As shown by the figures, the advantage of this invention mainly lies in its utmost simplicity and in that the patient may be carried to the proper examination position by substantially a single pivotal motion of the patient table or the patient bearing surface, which may be performed manually in a simple manner.

This advantage is enhanced by the fact that the patient bearing surface is considerably wider and/or longer than the average or maximum width and or the average or maximum height of patients.

The length of the patient bearing surface 102 is greater than the maximum or average height of patients by ¼ to ½ of such average or maximum height. This also substantially applies to the width of the patient table, which this time is greater than the maximum or average width of the patient by ¼ to ½.

Thanks to this feature, as shown in FIGS. 1 to 8, the patient may be asked to lie on the table in several different positions relative to the length and width of the patient table and even not parallel to the longitudinal axis of the patient table, i.e. inclined sideways or diagonally as particularly shown in FIG. 8. Conversely, FIG. 7 shows how the patient position is parallel to the longitudinal axis of the patient table but the patient is displaced sideways towards one of the longitudinal edges of the patient table.

A further feature consists in that the patient table has a patient bearing surface 102 with one portion extending substantially from the end associated to the vertical axis of oscillation to an area substantially coinciding with the magnet structure side S1 opposite to said end of the patient bearing surface 102 and is formed with a substantially symmetrical lateral convexity with respect to the central longitudinal axis and to the central transverse axis with reference to the distance from said end of the patient bearing surface associated to the vertical axis of oscillation O to said area coincident with the opposite side S1 of the magnet structure, and extends beyond said side S1 of the magnet structure opposite the vertical axis of oscillation with a small end portion of a substantially square and rectangular shape. As shown from the figures and particularly from FIGS. 7 to 10, the longitudinal sides of the convex portion of the patient bearing surface 102 are curved to such an extent and with such a shape that, in the oscillated position of such patient bearing surface 102 in which the latter abuts against the vertical wall member 301, the portion of the patient bearing surface 102 which abuts against said vertical wall member 301 is substantially parallel to said vertical wall member 301 along at least one half of the extension of the latter in the longitudinal direction of the patient bearing surface.

For accurate indication of the above positions of the patient, the receiving coils may be particularly used as a reference.

As shown, the patient table 2 of this invention has one or more receptacles for connection to one or more different receiving coils, which may be arranged in different patterns depending on the limb or anatomic regions where for they were designed and depending on the receiving coil type.

These coils are not shown in detail, because they are not part of the present invention except to the extent that they have a socket or one or more ends for connection with the patient bearing surface, e.g. as disclosed in EP 995 397 by the proprietor hereof.

In addition to the connection socket cooperating with one connection receptacle within the patient table surface, the receiving coils have a space for introduction of the limb or part of the patient body corresponding to the anatomic region under examination. On the other hand, other coil types, such as those for Magnetic Resonance Imaging of the spine are simply arranged adjacent the body part corresponding to such anatomic region.

In any case, the position of the patient relative to the patient table is defined by the position of the receiving coil on said patient table, which receiving coil is designed for a predetermined limb or a predetermined anatomic region and the position of the coil relative to the patient bearing surface is defined by the position on said patient bearing surface 102 of the corresponding receptacle for connection of the coil to such patient bearing surface 102.

FIGS. 10 to 14 show several different patterns of coils in connection receptacles 20, 21, 22, 23 for different receiving coils. With reference to such patterns of connection receptacles 20 to 23, it shall be noted that they are aligned along circular lines concentric with the vertical axis of oscillation O of the patient table and are coincident with at least one circular band concentric with said vertical axis of oscillation O and passing through the imaging volume VI.

Advantageously, considering the size and particular shape of the patient bearing surface 102 and the possibility to place the patient in several different positions on the patient table, e.g. upside down, the different patterns of receptacles for connection to the receiving coils have a common positioning constant, which consists in that all the receptacles are arranged along a circular line transverse to the patient bearing surface, which is concentric with the axis of oscillation O of the patient bearing surface and is coincident with a circular path coaxial to the vertical axis of oscillation O and which path falls within an annular band of the same width as the diameter of the imaging volume VI and passing there through. Advantageously, all coil connection receptacles 20, 21, 22, 23 are arranged along a single circular line transverse to the patient bearing surface, which is concentric with the axis of oscillation O of the patient bearing surface and coincident with a circular path coaxial with the vertical axis of oscillation O and which path passes through the central vertical axis of the imaging volume VI.

Obviously the connection receptacles 20, 21, 22, 23 may be also arranged in different positions from those described above, but such that the receiving coils, when mounted in these operative position receptacles, are arranged along said transverse circular line.

Thanks to this configuration, the patient table is very easily assembled, because the position marks of the various coils are limited to such single transverse circular line, which is designated by LC in FIGS. 10 and 11 and is perfectly coincident with the coaxial circular line passing through the center of the imaging volume VI.

The angular position of the holding receptacles 20, 21, 22, 24 is also such that each of these receptacles or each of these coils in one of the receptacles may be caused to coincide with the imaging volume VI by an angular motion of the patient table and the patient bearing surface 102.

In the morphology of the human body, the limbs are disposed symmetrically or substantially symmetrically with respect to the center axis of the body wherefore advantageously, in at least one configuration, the patient bearing surface has two identical holding receptacles arranged over said circular line LC and symmetrically to the central longitudinal axis, i.e. on each side of the opposite side of such center longitudinal axis of the patient bearing surface 102. Particularly, this arrangement is provided for the receiving coil receptacles 20, 21 associated to the anatomic regions of the foot, the ankle, the knee, the wrist, the hand, the elbow, the shoulder and other anatomic regions having similar symmetric arrangement. In this case, the receptacle 21 on the half of the patient bearing surface 102 opposite the vertical wall member is in such position that such receptacle and/or the receiving coil therein are coincident with the imaging volume VI at the latest when the patient bearing surface abuts against the vertical wall member 301 as shown in FIG. 10.

Conversely, concerning the coil for imaging the spine or anatomic regions of the central portion of the body, the receptacle/s 23 of these coils are coincident with the central longitudinal axis of the patient bearing surface 102 or with an axis parallel thereto. This pattern is also shown in FIG. 10. In this case, advantages are achieved by providing the vertical axis of oscillation O of the patient bearing surface 102 in such a position relative to the magnet structure 1 that such receptacle 23 or such coil associated to said receptacle is coincident with the imaging volume VI when the central longitudinal axis of the patient table is perpendicular to a vertical plane which intersects the two horizontal legs and the vertical leg of the magnet structure 1 and contains the central vertical axis of the imaging volume VI.

Referring to FIGS. 10 to 14, two types of patterns are substantially provided: a first pattern in which the patient bearing surface 102 only has two receptacles 20 and 21, each disposed on one of the two longitudinal halves of such patient bearing surface 102 symmetrically with respect to the central longitudinal axis and along the above circular line or anyway so that such position is taken by the coils when mounted in these receptacles 20 and 21. A second pattern in which one central receptacle 23 is provided for one coil or an intermediate, preferably central receptacle 22 and/or 23 is provided between these two receptacles 20 and 21, or such receptacle 22 and/or 23 is in such position that the corresponding coil is in a central position between the coils mounted in the side receptacles 20 and 21.

Further patterns of receiving coil receptacles are obviously envisageable, the ones mentioned above only having to be considered preferred selections in that they have the advantage of maximizing construction simplicity and cost reduction, without affecting convenient use and especially fast, simple and accurate patient positioning.

Referring to FIGS. 12 to 14, the invention provides a further advantageous feature in that the coil connecting receptacles 20, 21, 22, 23 having different relative positioning patterns are not fixed on the patient bearing surface 102, but these receptacles for connection of the coils to the patient bearing surface 102 are mounted on coil supporting elements 602, 702 which have means for attachment thereof to the patient bearing surface 102 in an identical predetermined position, the receiving coil receptacles 20, 21, 22, 23 being provided on these coil supporting elements 602, 702 in predetermined positions and such that, when the coil supporting elements 602, 702 are attached to the patient supporting surface 102 such receptacles are in their proper position, as mentioned above.

Multiple coil supporting elements may be further provided, each having a predetermined number of coil connection receptacles in a predetermined position and each of these coil supporting elements having means for attachment to the patient bearing surface 102 which are identical and in the same positions for each of these coil supporting elements.

The coil fastening or connecting receptacles 20, 21, 22, 23 are provided on coil supporting elements 602, 702 which are separated from the patient bearing surface of the patient table and can be removably attached to or on the patient bearing surface 102, for instance by providing that the coil supporting elements 602, 702 act as a closure for an aperture 802 in the patient bearing surface in a predetermined position. Connection may occur by shape fit and/or for instance using a tab perpendicularly protruding from side of the coil supporting element, which is provided as a plate, such tab engaging by shape fit in the aperture 802 of the patient bearing surface 102 and a peripheral extension of the plate that forms the coil supporting element 602, 703 overlaps the patient bearing surface similar to the press fit of a paint can lid or the like.

With reference to the illustrated embodiment, the patient bearing surface 102 of the patient table has at least one receptacle 802 for holding and/or connecting the coil supporting element 602, 702, which receptacle is accessible from the patient support side and which holding and/or connection receptacle is level with the patient bearing surface.

A number of construction variants are envisageable. In one variant, the receptacle/s 802 for holding and/or connecting the coil supporting element and/or the receptacle/s 22, 23 for connection of the coil/s on the coil supporting elements 602, 702 are provided level with the patient bearing surface of the patient table or above or below it, to such an extent that the receiving coil/s are arranged on the coil supporting element and on the patient bearing surface 102, directly above said patient bearing surface or at a certain level above the patient bearing surface or below the patient bearing surface.

According to yet another construction variant, not shown, there may be provided coil supporting elements of smaller size than the corresponding receptacles for such elements in the coil supporting surface, in combination with removable inserts for complementing said holding and/or connecting receptacles for the coil supporting elements and/or there are provided removable inserts for complementing the receptacles for fixation of the receiving coils on the coil supporting elements.

Finally, elements for supporting or positioning the body parts under examination are provided at the coil holding or connecting receptacles 20, 21, 22, 23, such as cushions or the like, to allow proper positioning of the body part under examination and these support and positioning elements are removably associated to the receiving coil supporting element.

The coil supporting elements and/or the receptacles for coil fixation or connection are in such positions and have receiving coil connecting receptacles in such positions that at least one receiving coil is located at one or both the shoulders and/or one or both elbows and/or one or more wrists and/or one or both hands and/or one or both knees and/or one or both ankles and/or at least part of the spine with the patient lying in a substantially central position on the patient bearing surface.

The advantages provided by the present invention in terms of posture and positioning of the patient are self-evident from FIGS. 1 to 9.

With the patient table outwardly pivoted, as shown in FIG. 1 and FIG. 9, the patient may lie on the patient table either from the side opposite the magnet structure or the side facing it. Furthermore, for patient positioning, the operators may operate alternately or even simultaneously from both opposite longitudinal sides of the patient table, thereby effectively assisting the patient to lie in the proper position and being able to work in pairs and have maximum accessibility to all patient table parts and to the patient receiving cavity.

The patient is moved into the patient receiving cavity with the receiving coil or the limb or anatomic region to be examined in a centered position with respect to the imaging volume VI by simply pivoting the patient table towards the magnet structure 1.

Once the receiving coil and the receptacle with which it is connected on the patient bearing surface are defined and once the vertical axis of oscillation O of the patient bearing surface is fixedly positioned relative to the magnet structure, predetermined marks and limit stops may be provided which operate in an automatic or semiautomatic fashion and may be triggered, for instance, by the receiving coil as it is mounted in the connecting receptacle thanks to automatic means controlled by the receiving coil socket.

As shown by the figures, most of these auxiliary automatic means may be omitted thanks to the fact that the patient may lie on the patient table in various positions and that the receiving coils always have a predetermined position relative to the axis of oscillation O of the patient bearing surface and hence to the imaging volume. Therefore, as noted above, the receiving coil required for a specific examination determines the position that the patient has to assume on the patient table with respect to the coil ad to the table itself, which is sufficient to provide a safe positioning reference for the receiving coil and the patient in an optimal coincidence position with the imaging volume, by simply pivoting the table through a predetermined angle.

FIG. 1 shows a patient table with a spine-specific receiving coil, which patient table also supports the patient in such a position that the lumbar spinal region falls, with the receiving coil, in the imaging volume.

Figure 3:
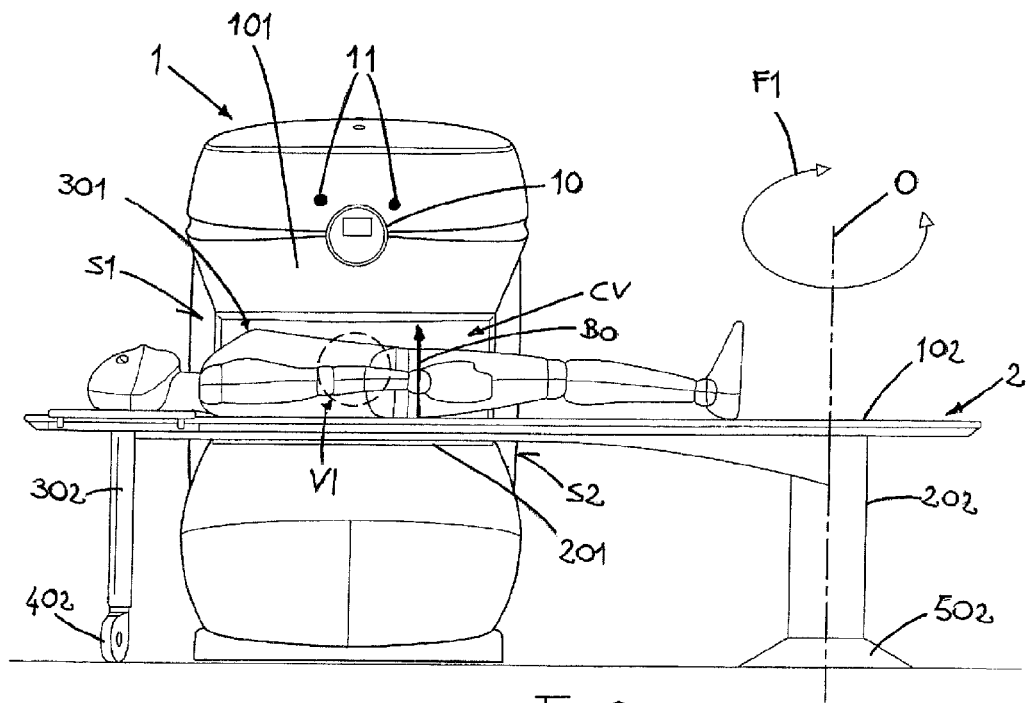
FIGS. 3 and 4 are two front views, i.e. of the front side of the MRI apparatus and of the longitudinal side of the patient table, with the patient in such position that the imaging volume contains the lumbar region of the spine and the cervical region of the spine respectively.
Figure 4:
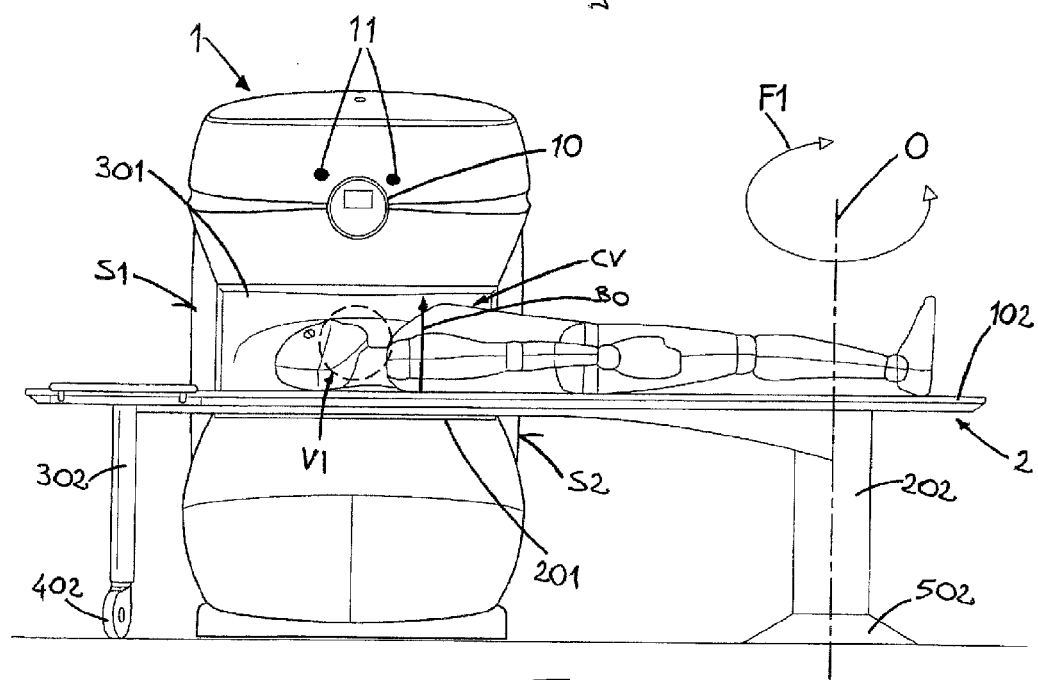

FIGS. 3 and 4 are side views that show the two patient positions with respect to the longitudinal extension of the patient table and to the position of the receiving coil for the spine, in which the patient of FIG. 3 is positioned as indicated with reference to FIG. 1, and the patient of FIG. 4 is staggered towards the end of the patient table associated to the axis of oscillation O, whereby his/her cervical spinal region correspond to the receiving coil and the imaging volume.

FIGS. 5 and 6 show the position of the patient on the patient table and relative to the receiving coil designed for imaging of the left knee, ankle or foot respectively. Here again, a single receptacle 21 is filled by a receiving coil which is brought to coincidence with the imaging volume by substantially identical angular displacements of the patient table for the two different anatomic regions. However, the patient has two different positions relative to the longitudinal extension of the patient table. The two configurations of the patient table, magnet structure and patient only differ from each other with respect to such patient position relative to the longitudinal extension of the patient table.

FIGS. 7 and 8 show a further patient positioning arrangement, in which the patient is not only moved in the longitudinal direction of the patient table, but also laterally or in a tilt direction relative to the longitudinal axis of the patient table.

Referring to FIGS. 1 to 8 and 15, the invention further provides the additional feature that the magnet structure 1 and particularly the front side of its upper horizontal leg supports a local display 10. Thanks to this screen, the images detected during positioning are displayed for the operators to check proper positioning of the patient and particularly the oscillation angle of the patient table directly using images detected at the patient position. Using low resolution modes real time or quasi real time imaging is possible. This allows omission of the automatic, semiautomatic or manual limit stops, which complicate construction and make it costly and of difficult use.

According to a further advantageous feature, in addition to display means 10, such as a small LCD screen, one, two or more input means, generally designated by numeral 11, may be provided on the front side of the magnet structure, which allow operators to adjust certain imaging parameters and/or store data and recall information from a memory, to simplify manual positioning operations and avoid the need for the operator to run or frequently move between the magnet structure and the MRI apparatus console.

Particularly, a central image generating section may be provided that has a memory which stores one or more magnetic resonance imaging sequences and/or one or more imaging parameter settings, associated to such sequences, which are adapted for real time or quasi real time position imaging.

The central image generating section comprises recall means of the software or electromechanical switch or selector type, for recalling the imaging settings and the imaging and display procedures of the position images, whereas one or more controls are provided on the magnet structure for recalling and/or selecting and/or implementing the procedures for imaging and displaying the position images and/or software procedures for selection and control of the central image generating section of the menu type, and selects and actuates (by pointing and clicking) for controlling and changing the position imaging settings.

These features may be also provided in MRI apparatus having different structures from those of the present invention, such as the one of FIG. 15, in which the patient bearing surface is composed of the lower horizontal wall member 201 of the magnet structure and a surface that forms an extension of this wall out of the patient receiving cavity CV.

FIGS. 9, 10 and 11 also provide dimensions for the patient table, the magnet structure, the angular width of oscillation of the patient table and the maximum space requirements for use of the inventive apparatus, to allow access and passage of the operators along all the sides of the apparatus and about 50° outward angular oscillation of the patient table.

As shown in FIG. 9, by providing minimum passages of about 500 mm on both end sides of the patient table and of 480 mm on the rear side of the apparatus as well as a 50° outward angular displacement with a length of about 2800 mm, the apparatus requires a space delimited by a 3800 m×3550 mm rectangle.

The above figures also show that the angle of oscillation of the patient table beyond the position in which the longitudinal axis of the patient table is parallel to or coincident with the axis that joins the central vertical axis of the imaging volume and/or the patient receiving cavity and/or the plan shape of the pole pieces to said axis of oscillation, is from 5° to 10°.

Therefore, the apparatus of the present invention allows the implementation of a method for positioning a patient therein, which comprises the steps of:

Positioning at least part of the patient table outside the patient receiving space delimited by the two opposite horizontal wall members by pivoting the patient table about a vertical axis of rotation outside the magnet structure, said rotation occurring in a direction away from the vertical support member for the two plates, Positioning the patient on the patient bearing surface for imaging at least one anatomic region, particularly for imaging anatomic regions of the foot, the knee, the hand, the shoulder, the spine and the head, Positioning the patient table in said patient receiving space for acquiring signals emitted from the anatomic region to be analyzed, by pivoting the patient table about a vertical axis of rotation outside the magnet structure, in a direction towards the vertical support member for the two opposite horizontal wall members.

The method may also include the step of pivoting the patient table into the imaging volume for imaging one or more anatomic regions, particularly for imaging anatomic regions from the right side to the left side of the body and vice versa.

For imaging of anatomic regions of right and/or left upper and/or lower limbs, the patient has to lie on the patient table with the upper and lower limbs in normal positions and/or slightly opened apart, and in a position in which the right and left limbs are on each side of the central median axis of the patient table respectively.

Automatic check of the position of the anatomic region to be examined in the imaging volume is carried out through the steps of positioning a receiving coil designed to detect signals from a predetermined anatomic region in a predetermined position on the patient table, positioning the axis of oscillation of the patient table in a predetermined manner with respect to the position within the space of the imaging volume VI and positioning the patient on said patient table with the anatomic region in a predetermined position relative to the receiving coil, the latter and the anatomic region being moved to coincidence with the imaging volume by angular displacement of the patient table about the vertical axis of oscillation.

FIG. 16 finally shows a particular construction of the shell that covers the magnet structure 1 of the apparatus of this invention. In this case, the shell that covers the upper and lower horizontal legs is composed of three parts separated along a central horizontal plane of the corresponding horizontal leg and having a rear extension for laterally covering the sides S1 and S2 of the magnet structure and particularly the corner areas for connection to the vertical member of the magnet structure. Thus, each of the two horizontal legs of the magnet structure is covered by two half-shells 30, 31, 32, 33, which are separated along the central or intermediate horizontal plane of the corresponding leg. Each of these half-shells is closed at three skirt sides and at a horizontal side.

The lower half-shell 31 of the upper horizontal leg and the upper half-shell 32 of the lower horizontal leg have a closed horizontal side which terminates at a certain distance from the rear edge and forms a recess 37 for the passage of the vertical member. The latter is covered by a U-shaped shell part 34, which extends over the front side and the two side walls, whereas the rear side is closed by a rear wall member 35. A bottom base 36 is provided for bearing the lower half-shell of the lower horizontal leg. The half-shells and other shell parts may be interconnected by various means such as screws, bolts or other removable fastener means.

FIG. 17 illustrates schematically a further embodiment in which in one diagnostic apparatus two MRI apparatus are integrated. Each one is constructed according to the above described single MRI apparatus. The particular way of displacing the patient table and the geometrical configuration of the single apparatus allows to have two MRI devices which occupies a very limited volume without being limited in the capabilities of freely positioning the patient in different positions relatively to the imaging volume for carrying out MRI of different anatomic regions.

The invention claimed is:

1. A Magnetic Resonance Imaging apparatus having an open U- or C-shaped magnet structure, the magnet structure comprising at least one vertical connection member for joining two horizontal wall members which lie one above the other and are supported in a cantilever fashion and which horizontal wall members are held in a predetermined spaced relationship by said vertical member, said vertical member being eccentrically connected to said two wall members at a side edge thereof, wherein said horizontal wall members and said vertical member delimit the upper and lower sides and at least a vertical side band of a patient receiving space for receiving at least one part of a patient body, said patient receiving space has three open sides, one frontal open side along the side edges of the horizontal wall members on the side of said horizontal wall members which is opposed to the side at which the vertical wall member is provided and two lateral open sides respectively along the edges of each of the two opposite sides of the said horizontal wall members which are oriented transversally to the said frontal open side of the patient receiving space, wherein the said horizontal wall members support means for generating a static magnetic field that permeates said patient receiving space;

wherein the apparatus further comprises a patient table, supported in an intermediate position between the two horizontal wall members, and lying slightly above the lower horizontal wall member, the said patient table having a bridge like construction comprising a length which is greater than its width and two opposite ends at each one of which an upright supporting element is provided;

the table being mounted with one end to the corresponding upright supporting element in a rotatable way around a vertical axis intersecting a longitudinal axis of the table, the upright supporting element on the opposite end of the table being slidable relatively to the ground along a circular path corresponding to the rotation of the table around the said vertical axis;

the upright supporting element which supports the table in a rotatable manner having means for being secured in a fixed relative position relatively to the magnet structure and in which position the extension of the lower wall member between the two edges along the two opposite lateral open sides of the patient receiving space and the distance from the upright supporting element which supports the table in a rotatable manner is less than the length of the patient table between the two upright supporting elements;

and the said patient table being rotatable relatively to the magnet structure with its longitudinal axis oriented transversally relatively to the two lateral open sides of the patient receiving space and to the edges of the horizontal wall members along which the said lateral open sides are provided and each end of the patient table with the corresponding upright supporting element lying outside of the magnet structure and of the patient receiving space on one of the lateral open sides of the patient receiving space;

wherein an intermediate part of the table lies over the lower horizontal wall member and the said intermediate part of the patient table;

wherein the extension of the upper and lower horizontal wall members in the direction of cantilever from the vertical wall member or in a direction transverse to the frontal open side of the patient receiving space is greater than the width of the said intermediate part of the patient receiving space;

wherein a limited region of the patient receiving space forming an imaging volume in which the static magnetic field has certain desired values of homogeneity, the said limited region having a predetermined position inside the patient receiving space and a predetermined distance from the vertical wall member and from the edges of the horizontal wall members at the lateral and at the frontal open sides; and the patient table having one or more receptacles for holding and/or connecting receiving coil supports and/or one or more compartments for connecting and/or holding receiving coils;

wherein the upright supporting element, supporting the table in a rotatable manner being placed relatively to the vertical wall element and to the frontal open side of the patient receiving space at such a distance from the said vertical wall member that it can be displaced angularly against the vertical wall element to an angular position in which when the longitudinal side edge of the table oriented towards the vertical wall member abuts with the said vertical wall member the longitudinal lateral side edge of the table opposed to the vertical wall member is still at least within the vertical projection of the imaging volume on the said table;

and at least some of said receptacles for holding and/or connecting receiving coil supports and/or said compartments for connecting and/or holding receiving coils, particularly for the receiving coils associated to limbs or anatomic regions on both right and left sides of the patient, and the receiving coils mounted or fitted in the receptacles for holding and/or connecting receiving coil supports and/or said compartments for connecting and/or holding receiving coils are positioned aligned along an axis perpendicular to the longitudinal axis of the patient table and or along a path having the shape of an arc or of a circle concentric with the vertical axis of rotation of the patient table which path passes through at least a portion of the imaging volume.

2. A Magnetic resonance imaging apparatus according to claim 1, wherein the length and the width of the patient supporting table are greater than the maximum length and width of the human body.

3. A Magnetic imaging apparatus according to claim 1, wherein means are provided for connecting one end of the patient table to the corresponding upright supporting element in an way that the table is rotatable around a vertical axis of rotation.

4. A Magnetic resonance imaging apparatus according to claim 1, wherein the upright supporting element at one end of the patient table supporting the table in a rotatable manner is placed in a position relatively to the magnet structure in which one longitudinal axis of the table passing through the vertical axis of rotation of the said patient table and through a vertical axis coincident with the center of a spherical or cylindrical imaging volume is oriented perpendicular to the central axis of the lower or upper horizontal wall member which is oriented perpendicular to at least one edge or to at least a secant or a tangent line to the said edge of the lower or upper horizontal wall member which edge is provided along the frontal open side of the patient receiving space or at the opposite edge where the vertical wall member is provided.

5. A Magnetic resonance imaging apparatus according to claim 4, wherein the longitudinal axis of the patient table is the central longitudinal axis, while a receptacle for holding and/or connecting receiving coil supports and/or a compartment for connecting and/or holding receiving coils is provided on each side of the said central longitudinal axis.

6. A Magnetic resonance imaging apparatus according to claim 1, wherein the patient table is slidable in the direction of its longitudinal axis being connected to each of the upright supporting elements by means of a slide, while receptacles for holding and/or connecting receiving coil supports and/or compartments for connecting and/or holding receiving coils, particularly for the receiving coils associated to limbs or anatomic regions on both right and left sides of the patient, and the receiving coils mounted or fitted in the said receptacles for holding and/or connecting receiving coil supports and/or in the said compartments for connecting and/or holding receiving coils are positioned aligned along at least two axis oriented perpendicular to the longitudinal axis of the patient table and or along at least two paths having the shape of an arc or of a circle concentric with the vertical axis of rotation of the patient table which axis and which paths have a different distance and/o radius from the axis of rotation of the patient table.

7. A Magnetic resonance imaging apparatus according to claim 1, wherein the upright supporting element for supporting the patient table in a rotatable way is displaceable by displacement means and can be locked in position by means for switching off or locking the displacement means or by position locking means.

8. A Magnetic resonance imaging apparatus according to claim 1, wherein at least some of the receptacles for holding and/or connecting receiving coil supports and/or at least part of the said compartments for connecting and/or holding receiving coils, particularly for the receiving coils associated to limbs or anatomic regions on both right and left sides of the patient are arranged on a separate coil supporting element which is a separated part from the patient table, the patient table having a predetermined slot or seat for the said coil supporting element and means being provided for removably connecting mechanically and/or electrically the said coils supporting element to the patient table.

9. A Magnetic resonance imaging apparatus according to claim 8, wherein a set of coils supporting elements is provided while the patient table is provided with two or more slots or seats for one or more of the said coil supporting elements each coil supporting element having a different kind and or a different distribution of the receptacles for holding and/or connecting receiving coil supports and/or at least part of the said compartments for connecting and/or holding receiving coils.

10. A magnetic resonance imaging apparatus according to claim 9, wherein at least part of the said coils supporting elements are interchangeable one with another at a corresponding slot or seat of the patient table.

11. A magnetic resonance imaging apparatus according to claim 9, wherein each coil supporting element has one or more receptacles for a specific kind of coil and/or a specific pattern of one or more coils, which receptacles have various positions on said coils supporting element and various positions with respect to the patient table in the mounted condition of the coil supporting element at the corresponding slot or seat on the patient table.

12. A magnetic resonance imaging apparatus according to claim 9, wherein one or at least two or more coil receptacles are provided on each coil supporting element, the said receptacles having identical or different shapes and/or sizes, to receive coils of different shapes and/or sizes, specifically designed for an anatomic region to be examined and/or to fit a specific patient size.

13. A magnetic resonance imaging apparatus according to claim 9, wherein the patient table has a patient bearing surface and the patient table has at least one slot or seat for one or more coil supporting elements which slot or seat is accessible from the patient support side and which slot or seat is level with the patient bearing surface of the patient table.

14. A magnetic resonance imaging apparatus according to claim 9, wherein the patient table has a patient bearing surface and the slots or seats for the coil supporting element and/or the receptacle/s for connection of the coil/s on the coil supporting elements are provided level with the patient bearing surface of the patient table.

15. A magnetic resonance imaging apparatus according to claim 9, wherein the patient table has a patient bearing surface and the slots or seats for the coil supporting element and/or the receptacle/s for connection of the coil/s on the coil supporting elements are provided above or below the patient bearing surface of the patient table to such an extent that the receiving coil/s are arranged on the coil supporting element and on the patient bearing surface, directly above said patient bearing surface or at a certain level above the patient bearing surface or below the patient bearing surface.

16. A magnetic resonance imaging apparatus according to claim 9, wherein the set of coil supporting elements comprises at least one coil supporting element of smaller size than the corresponding slot or seat one or more removable inserts being provided in combination for complementing said slot or seat on the patient table for the coil supporting elements.

17. A magnetic resonance imaging apparatus according to claim 9, wherein elements for supporting or positioning the body parts under examination are provided at the slots or seats for the coil supporting elements, such as cushions or the like, to allow proper positioning of the body part under examination and these support and positioning elements are removably associated to the receiving coil supporting elements.

18. A magnetic resonance imaging apparatus according to claim 11, wherein the coil supporting elements and the coil receptacles on the said coil supporting elements are in such positions that at least two receptacles for two receiving coils are located at a predetermined point of the longitudinal extension of the patient table and symmetrically with respect to one another relatively to the central longitudinal axis of the patient table at a predetermined distance one from the other, the said distance corresponding the mean distance of the shoulders and/or of the elbows and/or of the wrists and/or of the hands and/or of the knees and/or of the ankles of a human body lying in a substantially central position on the patient table and having the legs slightly divaricated with an angle between 5° and 30° and the arms stretched along the body, while at least one or more receptacles of one or more receiving coils are placed centered along the central longitudinal bearing of the patient table along the spine of a human body.

19. A magnetic resonance imaging apparatus according to claim 1, wherein the magnetic structure has the cross section of a double C or of a laid down H in which one vertical wall element is provided or two vertical elements are provided one against the other and in which the upper and the horizontal wall members protrude in a cantilever way from each side of the vertical wall element or of the two adjacent vertical elements forming two patient receiving spaces on the two opposite sides of the vertical wall element, to each one of which a patient table is associated.

20. A method for positioning at least one portion of a patient body part for a predetermined anatomic region to be examined in the imaging volume contained in a patient body or body part receiving space of a Magnetic Resonance Imaging apparatus, which apparatus comprises a magnet structure for delimiting said patient receiving space and generating a static magnetic field in said space, which magnet structure has an open U or C shape, in which at least one vertical member is provided for connection of two horizontal wall members which are disposed one above the other and are supported in a cantilever fashion and at a predetermined distance by said vertical member, which is connected eccentrically and particularly at a side edge, to said two wall members and which apparatus further comprises a patient table which is rotatable about a vertical axis outside the magnet structure, said method comprising the steps of:

Positioning at least part of the patient table outside the patient receiving space delimited by the two opposite horizontal wall members by pivoting the patient table about a vertical axis of rotation outside the magnet structure, said rotation occurring in a direction away from the vertical support member for the two plates;

Positioning the patient on the patient bearing surface for imaging at least one anatomic region, particularly for imaging anatomic regions of the foot, the knee, the hand, the shoulder, the spine and the head;

Positioning the patient table in said patient receiving space for acquiring signals emitted from the anatomic region to be analyzed, by pivoting the patient table about a vertical axis of rotation outside the magnet structure, in a direction towards the vertical support member for the two opposite horizontal wall members; and Pivoting the patient table into the imaging volume for imaging one or more anatomic regions, particularly for imaging anatomic regions from the right side to the left side of the body and vice versa.

21. A method as claimed in claim 20, wherein, at least a portion of the patient table or part of the patient's body is positioned outside the patient receiving space, the angle of oscillation of the patient table between the central longitudinal axis of the patient table and the axis for ideal connection of said vertical axis of rotation of the patient table to said central vertical axis of the imaging volume is of about 50°.

22. A method as claimed in claim 20, wherein, for imaging of anatomic regions of right and/or left upper and/or lower limbs, the patient has to lie on the patient table with the upper and lower limbs in normal positions and/or slightly opened apart, and in a position in which the right and left limbs are on each side of the central median axis of the patient table respectively.

23. A method as claimed in claim 20, further comprising a step of automatic check of the position of the anatomic region to be examined in the imaging volume.

* * * * *